US006372206B1

(12) United States Patent
Soos et al.

(10) Patent No.: US 6,372,206 B1
(45) Date of Patent: *Apr. 16, 2002

(54) ORALLY-ADMINISTERED INTERFERON-TAU COMPOSITIONS AND METHODS

(75) Inventors: Jeanne M. Soos, Lansdale, PA (US); Joel Schiffenbauer, Gaithersburg, MD (US); Howard Marcellus Johnson, Gainesville, FL (US)

(73) Assignee: University of Florida, Gainesville, FL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/616,904

(22) Filed: Mar. 15, 1996

Related U.S. Application Data

(63) Continuation-in-part of application No. 08/406,190, filed on Mar. 16, 1995, now Pat. No. 5,906,816, and a continuation-in-part of application No. 08/438,753, filed on May 10, 1995, now Pat. No. 5,705,363, which is a continuation-in-part of application No. 08/139,891, filed on Oct. 19, 1993, now abandoned, which is a continuation-in-part of application No. 07/847,741, filed on Mar. 9, 1992, now abandoned, which is a continuation-in-part of application No. 07/318,050, filed on Mar. 2, 1989, now abandoned, said application No. 08/139,891, is a continuation-in-part of application No. 07/969,890, filed on Oct. 30, 1992, now abandoned.

(51) Int. Cl.$^7$ .................... A61K 38/21; C07H 21/04; C07K 14/555; C12N 15/19

(52) U.S. Cl. .................. 424/85.4; 930/142; 435/69.51; 536/23.52; 530/324; 530/351

(58) Field of Search ................ 424/85.4; 530/324, 530/351; 930/142; 435/69.51; 536/23.52

(56) References Cited

U.S. PATENT DOCUMENTS

| 4,997,646 A | | 3/1991 | Hansen et al. |
|---|---|---|---|
| 5,019,382 A | * | 5/1991 | Cummins, Jr. |
| 5,206,219 A | | 4/1993 | Desai |
| 5,372,808 A | | 12/1994 | Blatt et al. |
| 5,705,363 A | * | 1/1998 | Imakawa |

FOREIGN PATENT DOCUMENTS

| WO | WO90/09806 | | 9/1990 |
|---|---|---|---|
| WO | WO 94/10313 | * | 5/1994 |
| WO | WO 95/27499 | * | 10/1995 |
| WO | WO 95/27502 | * | 10/1995 |

OTHER PUBLICATIONS

Brod et al. (b) J. Interferon. & Cytokine Res. 15:115–122, 1995.*
Brod et al. (c) Neurology 44: 1144–1148, 1994.*
Arnason et al. Clinical Neuropharmacology 17(6):495–547, 1994.*
Freshney, R. Ian Culture of Animal Cells: A Manual of Basic Technique, Alan R. Liss, Inc., NY, NY, pp. 3–4, 1983.*
Imakawa, Kazuhiko, et al., Interferon–like sequence of ovine trophoblast protein secreted by embryonic trophectoderm, Nature, vol. 330, pp. 377–379, Nov. 1987.*
Pontzer, Carol H., et al., Antiviral Activity of the Pregnancy Recognition Hormone Ovine Trophoblastt Protein–1, Biochem. Biophys. Res. Commun., vol 152, No. 2, pp. 801–807, Apr. 1988.*
Dermer, Gerald B., Another Anniversary for the War on Cancer, Bio/Technology, vol. 12, p. 320, Mar. 1994.*
Brod et al. Neurology 44:1144–1148, 1994.*
Arnason et al. Clinical Neuropharmacology, 17(6):495–547, 1994.*
Amidon, G.L., et al., *Peptide and Protein Drug Delivery* 43:146–152, (1998).
Anonymous, *Lancet* 336(8720):935 (1990).
Brod, S., et al., *J of Interferon and Cytokine Research* 15 (2):115–122 (1995).
Brod, S. and Khan, M., *J of Autoimmunity* 9(1):11–20 (1996).
Caban, J., et al., *Archivum Immunologiae et Therapiae Experimentalis* 41(3–4):229–235 (1993).
Cummins, J.M., et al., *Veterinary Immunology and Immunopathology* 45 (3–4):355–60 (1995).
Cummins, J.M., *J. Biol. Response Modif* 7(5):513–523 (1988).
Degre, M. and Bukholm, G., *J of Biological Regulators and Homeostatic Agents* 9(1):15–20 (1995).
Fleischmann, W., et al., *Proceedings of the Society for Experimental Biology and Medicine* 201(2):200–7 (1992).
Georgiades, J.A., *Archivum Immunologiae et Therapiae Experimentalis* 44(1):11–22 (1996).
Georgiades, J.A., *Archivum Immunologiae et Therapiae Experimentalis* 41(3–4):259–265 (1993).
Hutchinson, V.A., et al., *Mol Biother* 2(3):160–164 (1990).
Johnson, H.M, et al., *Scientific American* 270 (5):40–47 (1994).
Koren, S., et al., *Proceedings of the Society for Experimental Biology and Medicine* 204(2):155–164 (1993).
Lecce, J.G., et al., *Mol Biother* 2(4):211–216 (1990).
Moore, B., et al., *Veterinary Immunology and Immunopathology* 49(4):347–358 (1996).
Nelson, P.A., et al., *Annals of the New York Academy of Sciences*, 778:45–155 (1996).

(List continued on next page.)

Primary Examiner—Phuong T Bui
(74) Attorney, Agent, or Firm—Perkins Coie LLP

(57) ABSTRACT

The invention includes interferon-tau (IFNτ) pharmaceutical compositions useful for oral administration to treat autoimmune disorders (particularly multiple sclerosis), cell proliferative disorders and viral disease.

33 Claims, 6 Drawing Sheets

OTHER PUBLICATIONS

Pontier, C.H., et al., *Cancer Research* 51:5304–5307 (1991).

Qi, Y., et al., *Hum Antibod Hybridomas* 7(1):21–26 (1996).

Ranace, V.V. and Hollinger, M.A., *Drug Delivery Systems*, CRC Press Inc. Boca Raton, Florida pp. 127–128, 151 (1996).

Shiozawa, K., et al., *Arthritis & Rheumatism* 39(9):S63 (1996).

Weiss, R.C., et al., *J. Am. Vet. Med. Assoc.* 199(10):1477–1481 (1991).

Wills, R.J., et al., *Journal of Interferon Research* 4(3):399–409 (1984).

Witt, P., et al., *J of Interferon Research* 12(6):411–413 (1992).

Zielinska, W., et al., *Archivum Immunologiae et Therapiae Experimentalis* 41(3–4):241–251 (1993).

Soos, J.M., et al. "The Novel Type I Interferon Tau Prevents Development and Superantigen Reactivation of Experimental Allergic Encephalomyelitis in Mice Without Associated Toxicity," *FASEB J. Experimental Biol.* 9(4):Abs. No. 5940 (1995).

Brod, S.A., and Burns, D.K., "Suppression of Relapsing Experimental Autoimmune Encephalomyelitis in SJL/J Mouse by Oral Administration of Type I Interferons," *Neurology* 44:1144–1148 (1994).

Brod, S.A., et al., "Modification of Acute Experimental Autoimmune Encephalomyelitis in the Lewis Rat by Oral Administration of Type I Interferons," *J. Interferon Res.* 15:115–122 (1995).

Soos, J.M., and Johnson, H.M., "Type I Interferon Inhibition of Superantigen Stimulation: Implications for Treatment of Super–antigen–Associated Disease," *J. Interferon Res.* 15:39–45 (1995).

Soos, J.M., et al., "The IFN Pregnancy Recognition Hormone IFN–τ Blocks Both Development and Superantigen Reactivation of Experimental Allergic Encephalomyelitis Without Associated Toxicity," *J. Immunol.* 155:2747–2753 (1995).

\* cited by examiner

ORALLY-ADMINISTERED INTERFERON-TAU COMPOSITIONS AND METHODS

This application is a continuation-in-part of application Ser. No. 08/406,190 filed Mar. 16, 1995, now U.S. Pat. No. 5,906,816, and a continuation-in-part of application Ser. No. 08/438,753 filed May 10, 1995, now U.S. Pat. No. 5,705,363, which is a continuation-in-part of U.S. Ser. No. 08/139,891 filed Oct. 19, 1993, now abandoned, which is a continuation-in-part of application Ser. No. 07/847,741 filed Mar. 9, 1992, now abandoned, which is a continuation-in-part of application Ser. No. 07/318,050 filed Mar. 2, 1989, now abandoned, and said application Ser. No. 08/139,891 filed Oct. 19, 1993 is a continuation-in-part of application Ser. No. 07/969,890 filed Oct. 30, 1992, now abandoned.

This work was supported in part by grant number AI 25904 awarded by the National Institutes of Health. Accordingly, the United States Government has certain rights in this invention.

FIELD OF THE INVENTION

The present invention relates to orally-administered pharmaceutical compositions containing interferon-tau and methods of uses thereof.

REFERENCES

Ausubel, F. M., et al., in CURRENT PROTOCOLS IN MOLECULAR BIOLOGY, John Wiley and Sons, Inc., Media, Pa. (1988).

Bartol, F. F., et al., *Biol. Reprod.* 32:681–693 (1985).

Bayne, M. L., et al., *Gene* 66:235 (1988).

Bazer, F. W., et al., *J. Animal Sci.* 57(Supp. 2):425 (1983).

Bazer, F. W., et al., *J. Reproduction and Fertility* 76:841 (1986).

Bazer, F. W., et al., PCT Application publication No. WO 94/10313, published May 11, 1994.

Beames, et al., *Biotechniques* 11:378 (1991).

Benoit, P., et al., *J. Immunol.* 150(3):707 (1993).

Blatt, L. M., et al., U.S. Pat. No. 5,372,808, issued Dec. 13, 1994.

Bonnem, E. M., et al., *J. Bio. Response Modifiers* 3:580 (1984).

Clayman, C. B., Ed., AMERICAN MEDICAL ASSOCIATION ENCYCLOPEDIA OF MEDICINE (Random House, New York, N.Y.), 1991.

Cross, J. C., and Roberts, R. M., *Proc. Natl. Acad. Sci. USA* 88:3817–3821 (1991).

Davis, G. L., et al., *N. England J. Med.* 321:1501 (1989).

Davis, G. L., et al., *Theriogenology* 38:867 (1992).

Day, M. J., et al., *Clin. Immunol. Immunopathol.* 35(1):85–91 (1985).

Degre, M., *Int. J. Cancer* 14:699 (1974).

DeMaeyer, E., et al., in INTERFERONS AND OTHER REGULATORY CYTOKINES, John Wiley and Sons, New York (1988).

Dusheiko, G. M., et al., *J. Hematology* 3(Suppl. 2):S199 (1986).

Ecker, D. J., et al., *J. Biol. Chem.* 264:7715–7719 (1989).

Ernst, J. F., *DNA* 5:483 (1986).

Familetti, P. C., et al., *Meth. Enzymol.* 78:387 (1981).

Feher, Z., et al., *Curr. Genet.* 16:461 (1989).

Fent, K. and G. Zbinden, *Trnds. Pharm. Sci.* 56:1–26 (1987).

Figuero, F., et al., *Immunogenetics* 15(4):399–404 (1982).

Finter, N. B., et al., *Drugs* 42(5):749 (1991).

Fritz, R. B., et al., *J. Immunol.* 130(3):1024–1026 (1983).

Gelvin, S. B. and R. A. Schilperoot, *Plant Molecular Biology* (1988).

Gnatek, G. G., et al., *Biol. Reprod.* 41:655–664 (1989).

Godkin, J. D., et al., *J. Reprod. Fertil.* 65:141–150 (1982).

Hansen, P. J., et al., U.S. Pat. No. 4,997,646, issued Mar. 5, 1991.

Harlow, E., et al., in ANTIBODIES: A LABORATORY MANUAL, Cold Spring Harbor Laboratory Press, Cold Spring Harbor, N.Y. (1988).

Hitzeman, R. A., et al., U.S. Pat. No. 4,775,622, issued Oct. 4, 1988.

Helmer, S. D., et al., *J. Reprod. Fert.* 79:83–91 (1987).

IFNβ Multiple Sclerosis Study Group, *Neurology* 43(4):655 (1993).

Imakawa, K., et al., *Nature* 330:377–379 (1987).

Imakawa, K., et al., *Mol. Endocrinol.* 3:127 (1989).

Johnson, H. M., et al., *Sci. Am.* 270(5):40–47 (1994).

Kashima, H., et al., *Laryngoscope* 98:334 (1988).

Kemppainen, R. J., and Clark, T. P., *Vet. Clin. N. Am. Small Anim. Pract.* 24(3):467–476 (1994).

Klein, J., et al., *Immunogenetics* 17:553 (1983).

Kotzin, B. L., et al., *J. Exp. Med.* 265:1237 (1987).

Kristensen, A. T., et al., *J. Vet. Intern. Med.* 8(1):36–39 (1994).

Lider, et al., *J. Immunol.*, 142:148–752 (1989).

Ludwig, D. L., et al., *Gene* 132:33 (1993).

Martal, J., et al., *J. Reprod. Fertil.* 56:63–73 (1979).

Martin, E. W., in DISPENSING OF MEDICATION: A PRACTICAL MANUAL ON THE FORMULATION AND DISPENSING OF PHARMACEUTICAL PRODUCTS Mack Publishing Co., Easton, Pa. (1976).

Mullis, K. B., U.S. Pat. No. 4,683,202, issued Jul. 28, 1987.

Mullis, K. B., et al., U.S. Pat. No. 4,683,195, issued Jul. 28, 1987.

Oeda, K., et al., U.S. Pat. No. 4,766,068, issued Aug. 23, 1988.

Oldham, R. K., *Hospital Practice* 20:71 (1985).

Pearson, W. R. and Lipman, D. J., *PNAS* 85:2444–2448 (1988).

Pearson, W. R., Methods in *Enzymology* 183:63–98 (1990).

Pontzer, C. H., et al., *Cancer Res.* 51:5304 (1991).

Quesada, J. R., et al., *N. England J. Med.* 310:15 (1984).

Reilly, P. R., et al., in BACULOVIRUS EXPRESSION VECTORS: A LABORATORY MANUAL (1992).

Roberts, R. M., et al., *Endocrin. Rev.* 13:432–452 (1992).

Rutter, W. J., et al., U.S. Pat. No. 4,769,238, issued Sep. 6, 1988.

Sabin, E., et al., *Bio/Technology* 7:705–709 (1989).

Sambrook, J., et al., in MOLECULAR CLONING: A LABORATORY MANUAL, Second Edition, Cold Spring Harbor Laboratory, Cold Spring Harbor, N.Y. (1989).

Shaw, K. J., et al., *DNA* 7:117 (1988).

Shen, L. P., et al., *Sci. Sin.* 29:856 (1986).

Smith, P. K., et al., *Anal. Biochem.* 150:76 (1985).

Stewart, H. J., et al., *J. Endocrinol.* 115:R13 (1987).

Weiner, H., et al., *Ann. Rev. Immunol.* 12:809–837 (1994).

Weinstock-Guttman, B., et al., *Ann. Neurol.* 37:7–15 (1995).

Werner, L. L., et al., *Vet. Immunol. Immunopathol.* 8(1–2):183–192 (1985).

Whaley, A. E., et al., *J. Biol. Chem.* 269(14):10864–10868 (1994).

Wilson, et al., *Biology of Reproduction* 20(Supp. 1):101A, Abstract (1979).

Wraith, D. C., et al., *Cell* 59:247 (1989).

Wu, D. A., et al., *DNA* 10:201 (1991).

Zamvil, S. S., and Steinman, L., *Ann. Rev. Immunol.* 8:579–621 (1990).

BACKGROUND OF THE INVENTION

Conceptus membranes, or trophectoderm, of various mammals produce biochemical signals that allow for the establishment and maintenance of pregnancy (Bazer, et al., 1983). One such protein, ovine trophoblast protein-one (oTP-1), was identified as a low molecular weight protein secreted by sheep conceptuses between days 10 and 21 of pregnancy (Wilson, et al., 1979; Bazer, et al., 1986). The protein oTP-1 was shown to inhibit uterine secretion of prostaglandin $F_2$-alpha, which causes the corpus luteum on the ovary to undergo physiological and endocrinological demise in nonpregnant sheep (Bazer, et al., 1986). Accordingly, oTP-1 has antiluteolytic biological activity. The primary role of oTP-1 was assumed to be associated with the establishment of pregnancy. oTP-1 was subsequently found to (i) exhibit limited homology (50–70%) with interferon alphas (IFNα) of various species (Imakawa, et al., 1987), and (ii) bind to a Type I interferon receptor (Stewart, et al., 1987). Despite some similarities with IFNα, oTP-1 has several features that distinguish it from IFNα including the following: oTP-1's role in reproductive biochemistry (other interferons are not known to have any role in the biochemical regulation of reproductive cycles), oTP-1's cellular source—trophoblast cells (IFNα is derived from lymphocyte cells), oTP-1's size—172 amino acids (IFNα is typically about 166 amino acids), and oTP-1 is weakly inducible by viruses (IFNα is highly inducible by viruses). The International Interferon Society recognizes oTP-1 as belonging to an entirely new class of interferons which have been named interferon-tau (IFNτ). The Greek letter τ stands for trophoblast.

The interferons have been classified into two distinct groups: type I interferons, including IFNα, IFNβ, and IFNω (also known as IFNαII); and type II interferons, represented by IFNγ (reviewed by DeMaeyer, et al., 1988). In humans, it is estimated that there are at least 17 IFNα non-allelic genes, at least about 2 or 3 IFNβ non-allelic genes, and a single IFNγ gene.

IFNα's have been shown to inhibit various types of cellular proliferation. IFNα's are especially useful against hematologic malignancies such as hairy-cell leukemia (Quesada, et al., 1984). Further, these proteins have also shown activity against multiple myeloma, chronic lymphocytic leukemia, low-grade lymphoma, Kaposi's sarcoma, chronic myelogenous leukemia, renal-cell carcinoma, urinary bladder tumors and ovarian cancers (Bonnem, et al., 1984; Oldham, 1985). The role of interferons and interferon receptors in the pathogenesis of certain autoimmune and inflammatory diseases has also been investigated (Benoit, et al., 1993).

IFNα's are also useful against various types of viral infections (Finter, et al., 1991). Alpha interferons have shown activity against human papillomavirus infection, Hepatitis B, and Hepatitis C infections (Finter, et al., 1991; Kashima, et al., 1988; Dusheiko, et al., 1986; Davis, et al., 1989).

In addition, type I interferons are useful in treating autoimmune diseases such as multiple sclerosis (MS). In fact, IFNβ has been tested and approved by the U.S. Food and Drug Administration (FDA) as an MS therapy.

Significantly, however, the usefulness of IFNα's has been limited by their toxicity: use of interferons in the treatment of cancer, autoimmune disorders and viral disease has resulted in serious side effects, such as fever, chills, anorexia, weight loss, and fatigue (Pontzer, et al., 1991; Oldham, 1985). These side effects often require (i) the interferon dosage to be reduced to levels that limit the effectiveness of treatment, or (ii) the removal of the patient from treatment. Such toxicity has reduced the usefulness of these potent antiviral and antiproliferative proteins in the treatment of debilitating human and animal diseases.

The present invention provides methods of treatment for cancer, autoimmune diseases (such as MS) and for inhibiting cellular proliferation and viral infection. These methods do not have the toxic side effects associated with currently-used therapies, and employ a convenient route of administration.

SUMMARY OF THE INVENTION

In one aspect, the present invention includes an improvement in a method of treating a disease condition in a mammal (e.g., mouse, dog or human) responsive to treatment by interferon-tau (IFNτ). The improvement comprises orally administering a therapeutically-effective amount of IFNτ. The orally-administered IFNτ is preferably ingested by the mammal. In a general embodiment, the IFNτ is orally-administered at a dosage of between about $1\times10^5$ and about $1\times10^8$ units per day, preferably at a dosage of between about $1\times10^6$ and about $1\times10^7$ units per day. The IFNτ may be, for example, ovine IFNτ (OvIFNτ), e.g., a polypeptide having the sequence represented as SEQ ID NO:2, or a human IFNτ (HuIFNτ), e.g., a polypeptide having the sequence represented as SEQ ID NO:4 or SEQ ID NO:6.

In one embodiment, the disease condition is an immune system disorder, such as an autoimmune disorder (e.g., multiple sclerosis (MS), type I (insulin dependent) diabetes mellitus, lupus erythematosus, amyotrophic lateral sclerosis, Crohn's disease, rheumatoid arthritis, stomatitis, asthma, allergies or psoriasis). MS is particularly amenable to treatment using the methods of the present invention.

In another embodiment, the disease condition is a cell proliferation disorder, such as a cancer (e.g., hairy cell leukemia, Kaposi's Sarcoma, chronic myelogenous leukemia, multiple myeloma, superficial bladder cancer, skin cancer (basal cell carcinoma and malignant melanoma), renal cell carcinoma, ovarian cancer, low grade lymphocytic and cutaneous T cell lymphoma, and glioma).

In yet another embodiment, the disease condition is a viral disease (e.g., hepatitis A, hepatitis B, hepatitis C, non-A, non-B, non-C hepatitis, Epstein-Barr viral infection, HIV infection, herpes virus (EB, CML, herpes simplex), papilloma, poxvirus, picorna virus, adeno virus, rhino virus, HTLV I, HTLV II, and human rotavirus).

In another aspect, the invention includes a method of treating an autoimmune disorder in a subject (e.g., a human subject), by orally administering a therapeutically-effective amount of interferon-tau (IFNτ) to the subject. The orally-administered IFNτ is preferably ingested by the subject. Examples of autoimmune conditions amenable to treatment, dosages, and sources of IFNτ are as presented above.

The invention also includes a method of decreasing the severity or frequency of a relapse of multiple sclerosis (MS) in a human suffering from MS, by orally administering a therapeutically-effective amount of interferon-tau (IFNτ) to the human. Examples of dosages and sources of IFNτ are as presented above.

In another aspect, the invention includes a method of treating a cell proliferation disorder in a subject (e.g., a human subject), by orally administering a therapeutically-effective amount of interferon-tau (IFNτ) to the subject. The orally-administered IFNτ is preferably ingested by the subject. Examples of cell proliferation disorders amenable to treatment, dosages, and sources of IFNτ are as presented above.

In still another aspect, the invention includes a method of treating a viral disease in a subject (e.g., a human subject), by orally administering a therapeutically-effective amount of interferon-tau (IFNτ) to the subject. The orally-administered IFNτ is preferably ingested by the subject. Examples of viral diseases amenable to treatment, dosages, and sources of IFNτ are as presented above.

A further aspect of the invention includes a method of enhancing fertility in a female mammal (e.g., a human female), by orally administering a therapeutically-effective amount of interferon-tau (IFNτ) to the mammal. Examples of dosages and sources of IFNτ are as presented above.

These and other objects and features of the invention will become more fully apparent when the following detailed description is read in conjunction with the accompanying drawings.

BRIEF DESCRIPTION OF THE SEQUENCES

Figure 1:
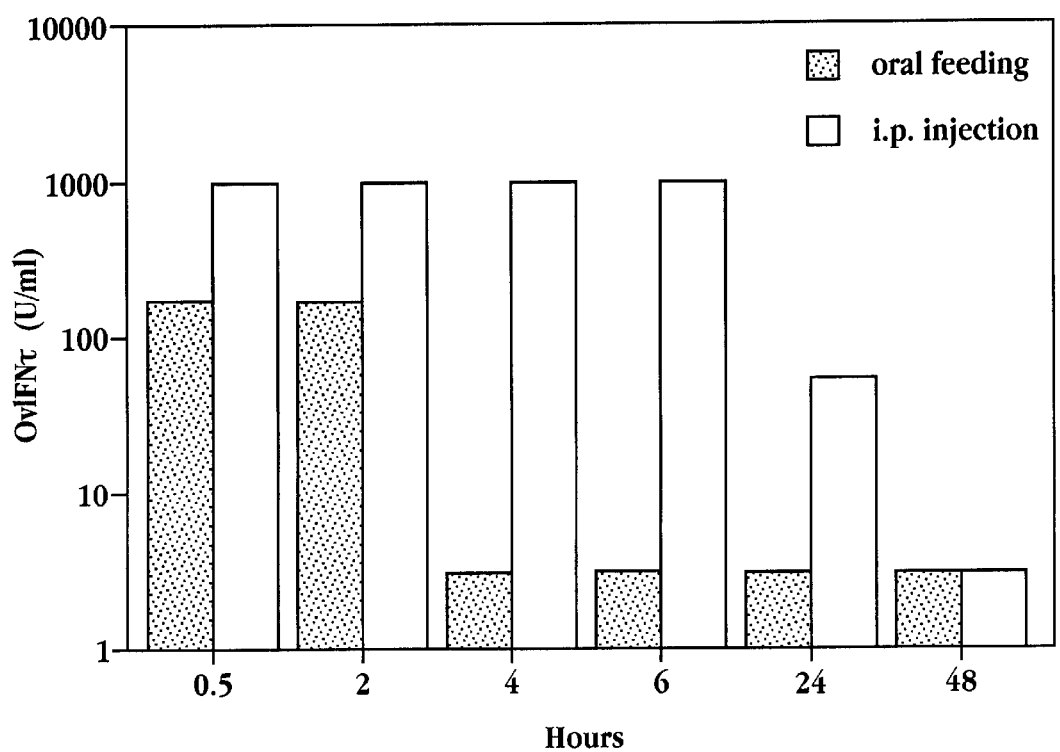
FIG. 1 shows the amount of OvIFNτ in NZW mouse sera after administration by either oral feeding (filled bars) or i.p. injection (open bars) as measured using an anti-viral assay.

SEQ ID NO:1 is the nucleotide sequence of a synthetic gene encoding ovine interferon-τ (OvIFNτ). Also shown is the encoded amino acid sequence.

SEQ ID NO:2 is an amino acid sequence of a mature OvIFNτ protein.

SEQ ID NO:3 is a synthetic nucleotide sequence encoding a mature human interferon-τ (HuIFNτ) protein.

SEQ ID NO:4 is an amino acid sequence for a mature HuIFNτT1 protein.

SEQ ID NO:5 is the nucleotide sequence, excluding leader sequence, of genomic DNA clone HuIFNτ3, a natural HuIFNτ gene.

SEQ ID NO:6 is the predicted amino acid sequence of a mature human IFNτ protein encoded by HuIFNτ3, encoded by the sequence represented as SEQ ID NO:5.

DETAILED DESCRIPTION OF THE INVENTION

Definitions

Interferon-τ refers to any one of a family of interferon proteins having at least one characteristic from each of the following two groups of characteristics: (i) (a) anti-luteolytic properties, (b) anti-viral properties, (c) anti-cellular proliferation properties; and (ii) about 45 to 68% amino acid homology with α-Interferons and greater than 70% amino acid homology to known IFNτ sequences (e.g., Ott, et al., 1991; Helmer, et al., 1987; Imakawa, et al., 1989; Whaley, et al., 1994; Bazer, et al., 1994). Amino acid homology can be determined using, for example, the LALIGN program with default parameters. This program is found in the FASTA version 1.7 suite of sequence comparison programs (Pearson and Lipman, 1988; Pearson, 1990; program available from William R. Pearson, Department of Biological Chemistry, Box 440, Jordan Hall, Charlottesville, Va.). IFNτ can be obtained from a number of sources including cows, sheep, ox, and humans.

An interferon-τ polypeptide is a polypeptide having between about 15 and 172 amino acids derived from an interferon-τ amino acid coding sequence, where said 15 to 172 amino acids are contiguous in native interferon-τ. Such 15–172 amino acid regions can also be assembled into polypeptides where two or more such interferon-τ regions are joined that are normally discontinuous in the native protein.

Treating a disease refers to administering a therapeutic substance effective to reduce the symptoms of the disease and/or lessen the severity of the disease.

II. Interferon-tau (IFNτ)

A. Introduction

The first IFNτ to be identified was ovine IFNτ (OvIFNτ). Several isoforms of the 18–19 kDa protein were identified in conceptus (the embryo and surrounding membranes) homogenates (Martal, et al., 1979). Subsequently, a low molecular weight protein released into conceptus culture medium was purified and shown to be both heat labile and susceptible to proteases (Godkin, et al., 1982). OvIFNτ was originally called ovine trophoblast protein-one (oTP-1) because it was the primary secretory protein initially produced by trophectoderm of the sheep conceptus during the critical period of maternal recognition in sheep. One isolate of mature OvIFNτ is 172 amino acids in length (SEQ ID NO:2).

IFNτS with similar characteristics and activities have been isolated from other ruminant species including cows and goats (Bartol, et al., 1985; Gnatek, et al., 1989; Helmer, et al., 1987; and Imakawa, et al., 1989). Bovine IFNτ (BoIFNτ) and OvIFNτ have (i) have similar functions in maternal recognition of pregnancy, and (ii) share a high degree of amino acid and nucleotide sequence homology between mature proteins. The nucleic acid sequence homology between OvIFNτ and BoIFNτ is 76.3% for the 5' non-coding region, 89.7% for the coding region, and 91.9% for the 3' non-coding region. The amino acid sequence homology is 80.4%.

Antisera to all the IFNτs cross-react. This is not unexpected since the species specific forms of IFNτ are more closely homologous to each other than to the IFNsα from the identical species (Roberts, et al., 1992). Relative to other interferons, OvIFNτ shares about 45 to 68% amino acid homology with Interferon-α and the greatest sequence similarity with the interferon-ωs (IFNωs) of about 68%.

TABLE 1

OVERVIEW OF THE INTERFERONS

| | Aspects | | | |
|---|---|---|---|---|
| | Type I | | | Type II |
| | Types | | | |
| | α & ω | β | τ | γ |
| | Produced by | | | |
| | leukocyte | fibroblast | trophoblast | lymphocyte |
| Effects: | | | | |
| Antiviral | + | + | + | + |
| Antiproliferative | + | + | + | + |
| Pregnancy Signally | − | − | + | − |

While IFNτ displays many of the activities classically associated with type I IFNs (see Table 1, above), considerable differences exist between it and the other type I IFNs. The most prominent difference is its role in pregnancy, detailed above. Also different is viral induction. All type I IFNs, except IFNτ, are induced readily by virus and dsRNA (Roberts, et al., 1992). Induced IFNα and IFNβ expression is transient, lasting approximately a few hours. In contrast, IFNτ synthesis, once induced, is maintained over a period of days (Godkin, et al., 1982). On a per-cell basis, 300-fold more IFNτ is produced than other type I IFNs (Cross and Roberts, 1991).

Other differences may exist in the regulatory regions of the IFNτ gene. For example, transfection of the human trophoblast cell line JAR with the gene for bovine IFNτ resulted in antiviral activity while transfection with the bovine IFNβ gene did not. This implies unique transacting factors involved in IFNτ gene expression. Consistent with this is the observation that while the proximal promoter region (from 126 to the transcriptional start site) of IFNτ is highly homologous to that of IFNα and IFNβ; the region from −126 to −450 is not homologous and enhances only IFNτ expression (Cross and Roberts, 1991). Thus, different regulatory factors appear to be involved in IFNτ expression as compared with the other type I IFNs.

IFNτ expression may also differ between species. For example, although IFNτ expression is restricted to a particular stage (primarily days 13–21) of conceptus development in ruminants (Godkin, et al., 1982), preliminary studies suggest that the human form of IFNτ is constitutively expressed throughout pregnancy (Whaley, et al., 1994).

B. Production of IFNτ

IFNτ polypeptides suitable for use in the methods of the present invention may produced in any of a number of ways. For example, they may be purified from animal tissues in which they are expressed, synthesized using a peptide synthesizer or produced recombinantly.

Recombinant IFNτ protein may be produced from any selected IFNτ polynucleotide fragment using a suitable expression system, such as bacterial or yeast cells. The isolation of IFNτ nucleotide and polypeptide sequences is described in Bazer, et al. (1994). For example, Bazer, et al., describe the identification and isolation of a human IFNτ gene. A synthetic nucleotide sequence encoding a mature human interferon-τ (HuIFNτ) protein is presented herein as SEQ ID NO:3. SEQ ID NO:4 is the corresponding amino acid sequence for a mature HuIFNτ1 protein. SEQ ID NO:5 is the nucleotide sequence, excluding leader sequence, of genomic DNA clone HuIFNτ3, a natural HuIFNτ gene, and SEQ ID NO:6 is the predicted amino acid sequence of a mature human IFNτ protein encoded by the sequence represented as SEQ ID NO:5.

To make an IFNτ expression vector, an IFNτ coding sequence (e.g, SEQ ID NO:1) is placed in an expression vector, e.g., a bacterial expression vector, and expressed according to standard methods. Examples of suitable vectors include lambda gt11 (Promega, Madison Wis.); pGEX (Smith, et al., 1985); pGEMEX (Promega); and pBS (Stratagene, La Jolla Calif.) vectors. Other bacterial expression vectors containing suitable promoters, such as the T7 RNA polymerase promoter or the tac promoter, may also be used. Cloning of the OvIFNτ synthetic polynucleotide into a modified pIN III omp-A expression vector is described in the Materials and Methods.

For the experiments described herein, the OvIFNτ coding sequence present in SEQ ID NO:1 was cloned into a vector, suitable for transformation of yeast cells, containing the methanol-regulated alcohol oxidase (AOX) promoter and a Pho1 signal sequence. The vector was used to transform *P. pastoris* host cells and transformed cells were used to express the protein according to the manufacturer's instructions.

Other yeast vectors suitable for expressing IFNτ for use with methods of the present invention include 2 micron plasmid vectors (Ludwig, et al., 1993), yeast integrating plasmids (YIps; e.g., Shaw, et al., 1988), YEP vectors (Shen, et al., 1986), yeast centromere plasmids (YCps; e.g., Ernst, 1986), and other vectors with regulatable expression (Hitzeman, et al., 1988; Rutter, et al., 1988; Oeda, et al., 1988). Preferably, the vectors include an expression cassette containing an effective yeast promoter, such as the MFα1 promoter (Ernst, 1986; Bayne, et al., 1988, GADPH promoter (glyceraldehyde-3-phosphate-dehydrogenase; Wu, et al., 1991) or the galactose-inducible GAL10 promoter (Ludwig, et al., 1993; Feher, et al., 1989; Shen, et al., 1986). The yeast transformation host is typically *Saccharomyces cerevisiae*, however, as illustrated above, other yeast suitable for transformation can be used as well (e.g., *Schizosaccharomyces pombe, Pichia pastoris* and the like).

Further, a DNA encoding an IFNτ polypeptide can be cloned into any number of commercially available vectors to generate expression of the polypeptide in the appropriate host system. These systems include the above described bacterial and yeast expression systems as well as the following: baculovirus expression (Reilly, et al., 1992; Beames, et al., 1991; Clontech, Palo Alto Calif.); plant cell expression, transgenic plant expression (e.g., Gelvin and Schilperoot, 1988), and expression in mammalian cells (Clontech, Palo Alto Calif.; Gibco-BRL, Gaithersburg Md.). These recombinant polypeptides can be expressed as fusion proteins or as native proteins. A number of features can be engineered into the expression vectors, such as leader sequences which promote the secretion of the expressed sequences into culture medium. The recombinantly produced polypeptides are typically isolated from lysed cells or culture media. Purification can be carried out by methods known in the art including salt fractionation, ion exchange chromatography, and affinity chromatography. Immunoaffinity chromatography can be employed, as described above, using antibodies generated based on the IFNτ polypeptides.

In addition to recombinant methods, IFNτ proteins or polypeptides can be isolated from selected cells by affinity-based methods, such as by using appropriate antibodies. Further, IFNτ peptides may be chemically synthesized using methods known to those skilled in the art.

III. Effectiveness of Orally-Administered IFNτ

Experiments performed in support of the present invention and detailed below demonstrate that orally-administered IFNτ polypeptide compositions are comparable in efficacy to injected IFNτ compositions with respect to the treatment of diseases or disease conditions which benefit from treatment with IFNτ.

Not only was orally-administered IFNτ effective at treating a disease benefiting from IFNτ treatment (EAE), but the oral route of administration resulted in unexpected advantages relative to treatment with injected IFNτ compositions. For example, orally-administered IFNτ resulted in a significantly lower level of anti-IFNτ antibodies in the serum of treated individuals (see Example 7). This is beneficial because the orally-administered IFNτ is therefore less likely to be rendered ineffective by a host immune response (i.e., desensitization to the treatment and/or dose level is significantly decreased), and the individual receiving the treatment is less likely to suffer adverse side effects as a result of such an immune response.

Results of experiments demonstrating these and related findings are presented below.

A. Orally-Administered IFNτ Inhibits Development of EAE

The efficacy of IFNτ in treating autoimmune disorders may be evaluated in rodents with experimental allergic encephalomyelitis (EAE; Zamvil and Steinman, 1990), an animal model of antigen-induced autoimmunity. EAE resembles human multiple sclerosis (MS) both in its clinical and pathological manifestations and can thus be used to assess treatments for human autoimmune diseases such as MS. EAE is a T-cell-mediated inflammatory autoimmune demyelinating disease induced by immunizing susceptible mouse, rat or guinea pig strains with myelin basic protein (MBP) or with encephalitogenic peptide fragments. Genetic susceptibility in the model animal strains is based in part on the capacity of encephalitogenic peptides to bind to particular class II major histocompatibility complex (MHC-II) molecules (Fritz, et al., 1983; Wraith, et al., 1989). In particular, mice having the H-$2^u$ haplotype are susceptible to EAE. Susceptible mouse strains include PL/J mice (Klein, et al., 1983), (PL/JxSJL)$F_1$ mice (Zamvil and Steinman, 1990; Wraith, et al., 1989), B10.PL mice (Figuero, et al., 1982), NZW mice (Kotzin, et al., 1987), and (NZBxNZW)F1 (Kotzin, et al., 1987) mice.

Gamma-interferon (IFNτ) and beta-interferon (IFNβ) have been demonstrated to be effective in treating multiple sclerosis (Johnson, et al., 1994; IFNβ Multiple Sclerosis Study Group, 1993). In fact, IFNβ has been approved by the FDA as a therapeutic for multiple sclerosis. Although β-IFN is effective against MS, it has relatively high toxicity, and as a result, has a variety of undesirable side effects. As described herein, however, IFNτ has significantly lower toxicity that other interferons and may therefore exhibit fewer undesirable side effects.

In experiments performed in support of the present invention and detailed in Example 1, orally-administered and injected IFN-τ was tested for its ability to prevent the induction of EAE. EAE was induced in New Zealand White (NZW) mice by immunization with bovine myelin basic protein (bMBP). Recipient NZW mice received OvIFNτ by either i.p. injection or oral feeding 48 hours prior to, on the day of, and 48 hours after immunization with bovine myelin basic protein (bMBP) for induction of experimental allergic encephalomyelitis (EAE).

Both oral feeding and i.p. injection of OvIFNτ protected against EAE (Example 1, Table 3). All animals that received IFNτ via i.p. injection, and 7 of 9 animals that received IFNτ orally, were protected from symptoms of EAE. Furthermore, anti-OvIFNτ monoclonal antibody HL127 was effective at partially neutralizing the ability of the OvIFNτ to block EAE. These experiments demonstrate that orally-administered IFNτ is effective in treating symptoms of EAE, an animal model of multiple sclerosis.

B. OvIFNτ is Present in Sera Following Oral Administration.

To confirm that orally-administered IFNτ enters the circulation, the sera of mice that received IFNτ by i.p injection or by oral administration were tested for the presence of IFNτ using a cytopathic effect (antiviral) assay (Familetti, et al., 1981) as described in Example 2.

The results are shown in FIG. 1. Specific activities are expressed in antiviral units/mg protein obtained from antiviral assays using MDBK cells. OvIFNτ was detected for up to two 2 hours following oral feeding (filled bars) at levels of 200 U/ml. These data indicate that orally-administered IFNτ enters the circulation and remains in serum for about two hours after being administered.

C. Lack of Toxicity from Orally-administered OvIFNτ

It has been previously demonstrated that the type I IFNs IFNα and IFNβ induced toxic side effects manifested as flu like symptoms, fever, nausea and malaise when used as therapeutics in humans (Degre, 1974; Fent and Zbinden, 1987). In contrast, OvIFNτ exhibits a remarkable lack of toxicity both in vitro and in vivo. Experiments performed in support of the present invention compared OvIFNτ with IFNs α and β for induction of toxicity as measured by lymphocyte depression in peripheral blood when given via oral feeding. Blood was obtained from the tail and white blood cells (WBC) counts were enumerated using a hemocytometer. Differential WBC counts were performed on Wright-Giemsa-stained blood smears.

The results are shown in Tables 2a, 2b and 2c, below. Significant levels of toxicity were detected in mice fed either IFN α and β while no significant lymphocyte depression was detected in mice fed $10^5$, $2\times10^5$ or $5\times10^5$ U of OvIFNτ or PBS alone. These data suggest that orally-administered OvIFNτ has significantly-reduced toxicity with respect to other type I IFNs.

Tables 2a–2c

Comparison of IFNs τ, β and α for Toxicity After Oral Feeding

TABLE 2a

| IFN | CELL COUNT (CELL NO. × $10^3$) BEFORE ORAL FEEDING | |
|---|---|---|
| (DOSE) | TOTAL WBC | LYMPHOCYTES |
| PBS | 7.0 ± 1.4 | 6.1 ± 1.2 |
| τ($10^5$) | 7.5 ± 0.7 | 6.4 ± 0.6 |
| τ(2 × $10^5$) | 6.5 ± 0.7 | 5.3 ± 0.6 |
| τ(5 × $10^5$) | 7.5 ± 0.7 | 6.5 ± 0.6 |
| β($10^5$) | 7.0 ± 0.7 | 5.9 ± 1.2 |
| β(2 × $10^5$) | 7.5 ± 2.1 | 6.5 ± 1.8 |
| α($10^5$) | 7.5 ± 0.7 | 6.6 ± 0.6 |

TABLE 2b

| IFN (Dose) | CELL COUNT (CELL No. × 10³) 18 H AFTER ORAL FEEDING | | |
|---|---|---|---|
| | TOTAL WBC | LYMPHOCYTES | % LYMPHOCYTE DEPRESSION |
| PBS | — | — | — |
| τ(10⁵) | 7.0 ± 1.4 | 6.0 ± 1.3 | 6.2 |
| τ(2 × 10⁵) | 7.0 ± 2.8 | 5.9 ± 2.4 | 0 |
| τ(5 × 10⁵) | 7.5 ± 2.1 | 6.3 ± 1.8 | 3.1 |
| β(10⁵) | 6.5 ± 0.7 | 5.1 ± 0.6 | 13.6 |
| β(2 × 10⁵) | 6.5 ± 0.7 | 4.1 ± 0.4† | 37.0 |
| α(10⁵) | 6.5 ± 2.1 | 4.7 ± 1.6 | 28.8 |

†p<0.05

TABLE 2c

| IFN (DOSE) | CELL COUNT (CELL No. × 10³) 24 H AFTER ORAL FEEDING | | |
|---|---|---|---|
| | TOTAL WBC | LYMPHOCYTES | # LYMPHOCYTE DEPRESSION |
| PBS | 7.5 ± 0.7 | 6.4 ± 0.6 | 0 |
| τ(10⁵) | 8.0 ± 2.8 | 6.9 ± 2.4 | 0 |
| τ(2 × 10⁵) | 7.0 ± 1.4 | 6.0 ± 1.1 | 0 |
| τ(5 × 10⁵) | 8.0 ± 4.2 | 7.0 ± 3.6 | 0 |
| β(10⁵) | 6.5 ± 3.5 | 5.1 ± 2.8 | 13.6 |
| β(2 × 10⁵) | 6.5 ± 0.7 | 4.0 ± 0.4† | 38.5 |
| α(10⁵) | 7.0 ± 0 | 5.0 ± 0† | 24.2 |

†p<0.05
‡p<0.03

D. OvIFNτ Prevents Chronic Relapse of EAE

Figure 2A:
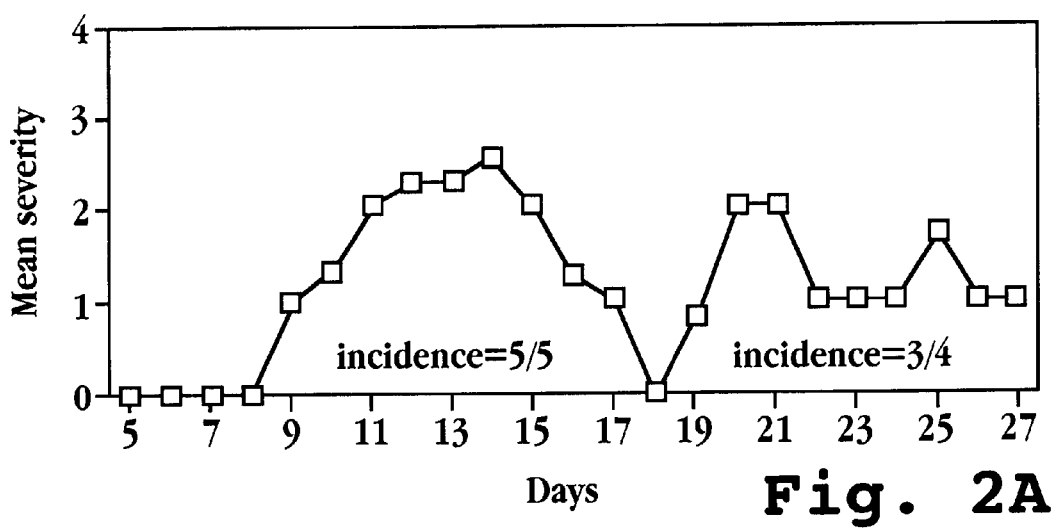
FIGS. 2A, 2B and 2C show the prevention of chronic-relapsing experimental allergic encephalomyelitis (EAE) in SJL mice by orally-administered (FIG. 2C) and i.p.-injected (FIG. 2B) IFNτ as compared with mice receiving no treatment (FIG. 2A).
Figure 2B:
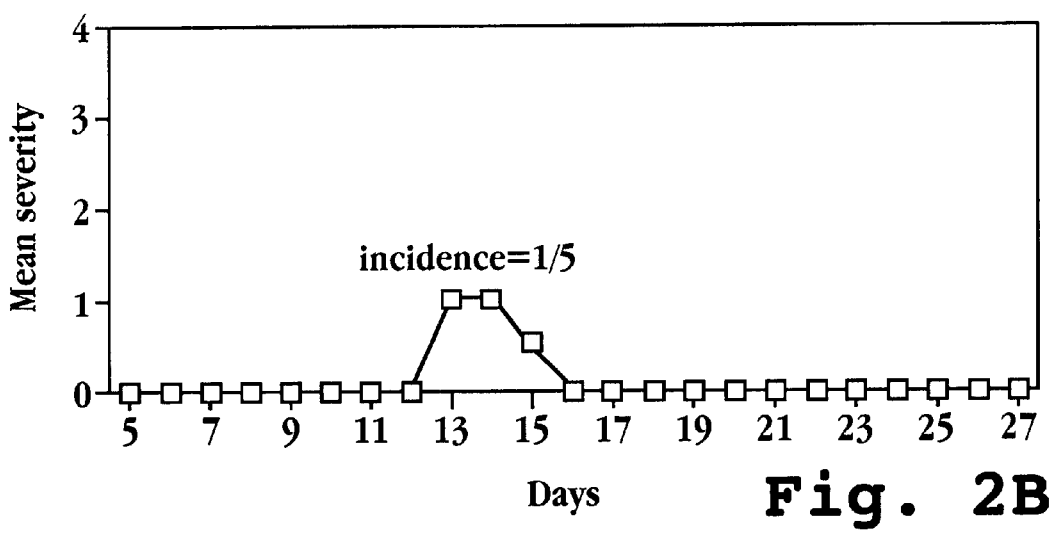
Figure 2C:
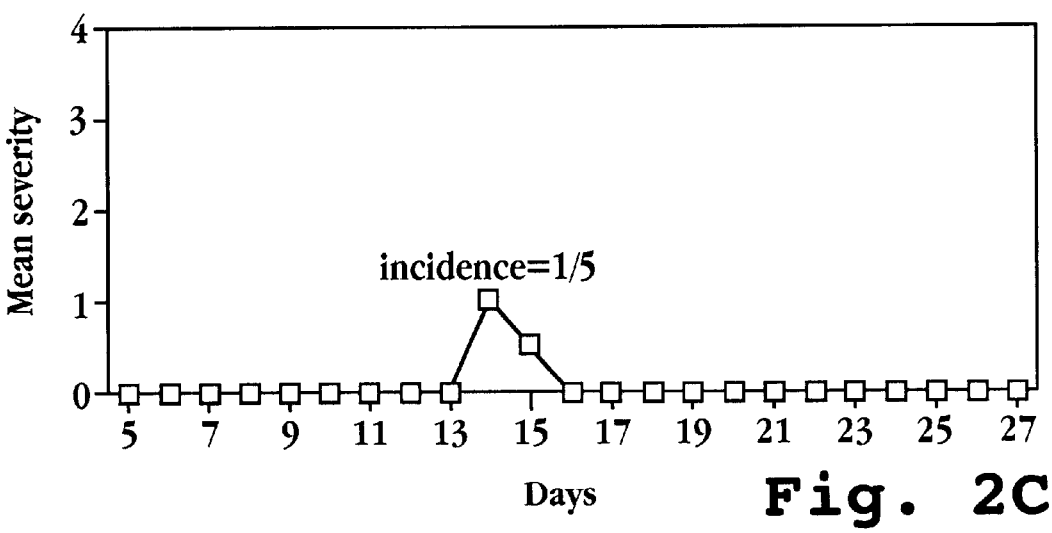

In addition to preventing the onset of symptoms associated with EAE, orally-administered OvIFNτ prevents paralysis in a chronic-relapsing model of EAE, as detailed in Example 3. Whereas 5/5 mice immunized with MBP (to induce EAE) which did not receive OvIFNτ treatment developed chronic relapsing paralysis, 4/5 animals treated with OvIFNτ (either i.p. injection or oral feeding, administered every 48 hours) were fully protected from the disease (FIGS. 2B and 2C). These data further support the results described above, and indicate that oral administration of IFNτ can block the development of chronic relapsing EAE. The experiments also suggest that orally-administration of IFNτ as infrequently as once every 48 hours, over an extended period of time, is as effective as i.p. injection at treating a disease condition responsive to treatment by interferon-tau.

E. Histological Analyses of Spinal Chord from EAE Mice following Oral Administration of IFNτ.

The ability of OvIFNτ to prevent EAE was also assayed by analyzing the effect of OvIFNτ treatment on cellular consequences of the disease, manifested in the central nervous system (CNS) as lymphocytic lesions in spinal cord white matter. The lesions are indicative of the extent of lymphocyte infiltration into the CNS. MBP-immunized mice were either not treated (control) or treated with OvIFNτ by oral or i.p. routes, and sections of the spinal cord lumbar region were stained and evaluated for lymphocytes as described in Example 4. Lymphocytic lesions were present in spinal cord white matter of control animals (FIG. 3A), but not in mice treated with OvIFNτ by i.p. injection (FIG. 3B) or oral feeding (FIG. 3C). These data indicate that the protective effect of IFNτ is associated with inhibition of lymphocyte infiltration of the CNS. Further, the data demonstrate that IFNτ treatment inhibits cellular manifestation of the autoimmune disease, rather than simply masking symptoms.

F. Cessation of Treatment with OvIFNτ Results in Relapsing Paralysis.

Figure 5:
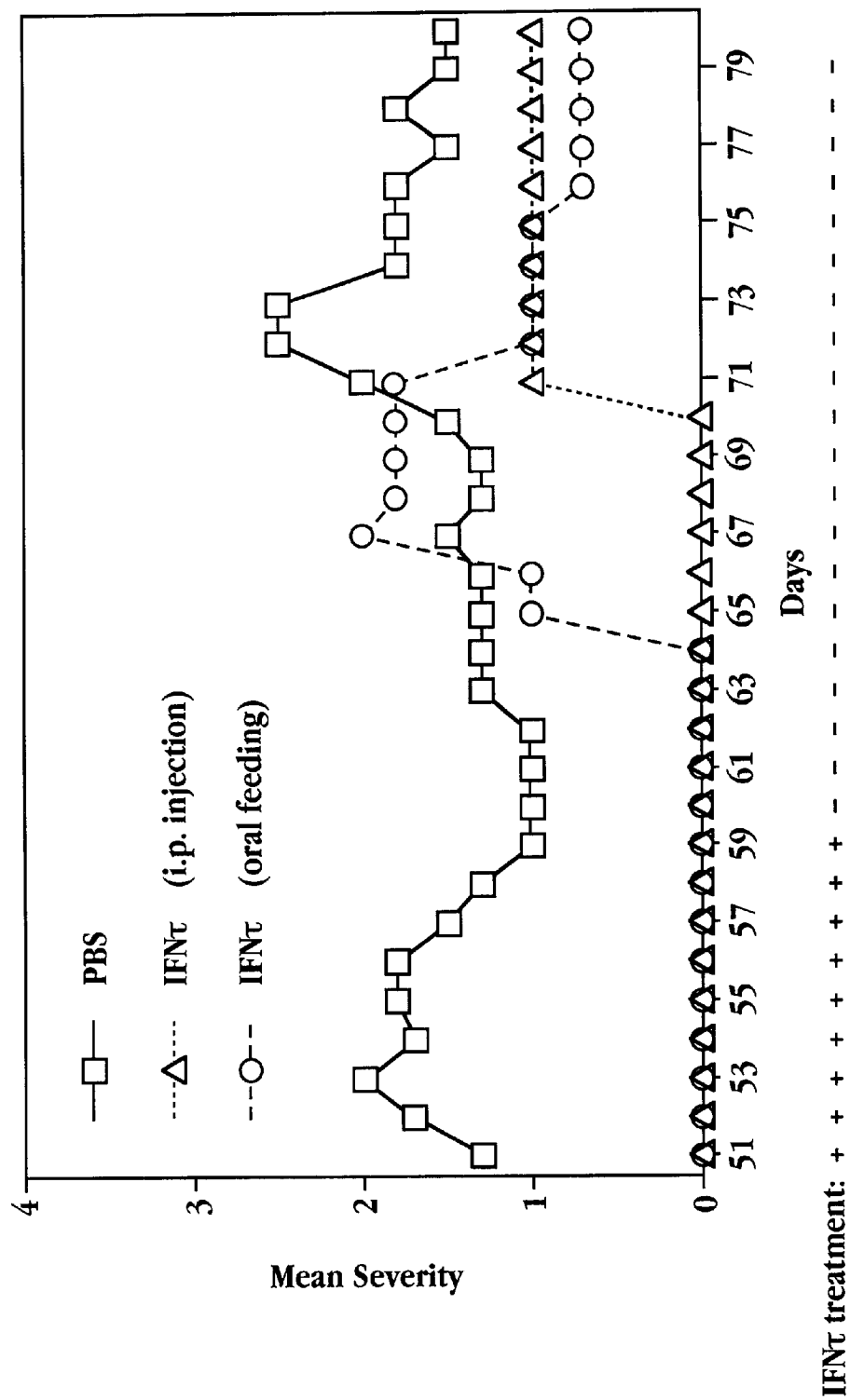
FIG. 5 shows relapses of EAE in SJL mice following removal of IFNτ treatment.

Experiments detailed in Example 6 were performed to determine the type and duration of treatment effective to prevent EAE in mice injected with MBP. The mice were protected from EAE by OvIFNτ treatment via i.p. injection or oral feeding (every 48 hours) as long as the treatment persisted (58 days in Example 6), but developed symptoms of the disease after OvIFNτ treatment was stopped (FIG. 5). These results suggest that while IFNτ may not cure an autoimmune condition like EAE (e.g., MS), it is an effective treatment that inhibits the pathological manifestations of the condition so long as treatment is continued.

G. Oral Administration of OvIFNτ Reduces Anti-OvIFNτ Antibody Response.

As detailed in Example 7, one advantage of orally-administered (as opposed to injected) IFNτ treatment is a reduction in the anti-IFNτ antibody titer in individuals receiving the oral treatment. After removal of OvIFNτ treatment, mice from each treatment group were bled and sera were examined for the presence of anti-OvIFNτ antibodies by ELISA. Whereas mice receiving IFNτ by i.p. injection exhibited elevated levels of anti-IFNτ antibodies, animals receiving IFNτ by oral feeding exhibited much lower anti-IFNτ antibody titers (typically 3 to 5-fold lower). As expected mice which received no OvIFNτ treatment displayed no anti-OvIFNτ antibodies.

The sera were also examined for their ability to neutralize OvIFNτ antiviral activity on the MDBK cell line. None of the sera from either i.p. injected or orally fed mice possessed neutralizing activity (Table 4). These results suggest that oral feeding of OvIFNτ largely circumvents an antibody response directed against the OvIFNτ protein. Such a reduced antibody response in orally-treated subjects reduces the chance of undesirable immune system-related side effects of IFNτ treatment.

IV. Applications

A. IFNτ as a Treatment for Immune System Disorders

Diseases which may be treated using methods of the present invention include autoimmune, inflammatory, proliferative and hyperproliferative diseases, as well as cutaneous manifestations of immunologically mediated diseases. In particular, methods of the present invention are advantageous for treating conditions relating to immune system hypersensitivity. There are four types of immune system hypersensitivity (Clayman, 1991). Type I, or immediate/anaphylactic hypersensitivity, is due to mast cell degranulation in response to an allergen (e.g., pollen), and includes asthma, allergic rhinitis (hay fever), urticaria (hives), anaphylactic shock, and other illnesses of an allergic nature. Type II, or autoimmune hypersensitivity, is due to antibodies that are directed against perceived "antigens" on the body's own cells. Type III hypersensitivity is due to the formation of antigen/antibody immune complexes which lodge in various tissues and activate further immune responses, and is responsible for conditions such as serum sickness, allergic alveolitis, and the large swellings that sometimes form after booster vaccinations. Type IV hypersensitivity is due to the release of lymphokines from sensitized T-cells, which results in an inflammatory reaction. Examples include contact dermatitis, the rash of measles, and "allergic" reactions to certain drugs.

The mechanisms by which certain conditions may result in hypersensitivity in some individuals are generally not well understood, but may involve both genetic and extrinsic factors. For example, bacteria, viruses or drugs may play a role in triggering an autoimmune response in an individual who already has a genetic predisposition to the autoimmune disorder. It has been suggested that the incidence of some types of hypersensitivity may be correlated with others. For example, it has been proposed that individuals with certain common allergies are more susceptible to autoimmune disorders.

Autoimmune disorders may be loosely grouped into those primarily restricted to specific organs or tissues and those that affect the entire body. Examples of organ-specific disorders (with the organ affected) include multiple sclerosis (myelin coating on nerve processes), type I diabetes mellitus (pancreas), Hashimotos thyroiditis (thyroid gland), pernicious anemia (stomach), Addison's disease (adrenal glands), myasthenia gravis (acetylcholine receptors at neuromuscular junction), rheumatoid arthritis (joint lining), uveitis (eye), psoriasis (skin), Guillain-Barré Syndrome (nerve cells) and Grave's disease (thyroid). Systemic autoimmune diseases include systemic lupus erythematosus and dermatomyositis.

Other examples of hypersensitivity disorders include asthma, eczema, atopical dermatitis, contact dermatitis, other eczematous dermatitides, seborrheic dermatitis, rhinitis, Lichen planus, Pemplugus, bullous Pemphigoid, Epidermolysis bullosa, uritcaris, angioedemas, vasculitides, erythemas, cutaneous eosinophilias, Alopecia areata, atherosclerosis, primary biliary cirrhosis and nephrotic syndrome. Related diseases include intestinal inflammations, such as Coeliac disease, proctitis, eosinophilia gastroenteritis, mastocytosis, inflammatory bowel disease, Chrohn's disease and ulcerative colitis, as well as food-related allergies.

Autoimmune diseases particularly amenable for treatment using the methods of the present invention include multiple sclerosis, type I (insulin dependent) diabetes mellitus, lupus erythematosus, amyotrophic lateral sclerosis, Crohn's disease, rheumatoid arthritis, stomatitis, asthma, uveitis, allergies and psoriasis.

Methods of the present invention may be used to therapeutically treat and thereby alleviate autoimmune disorders such as those discussed above. These treatments are exemplified herein with respect to the treatment of EAE, an animal model for multiple sclerosis.

B. IFNτ as Treatment for Reproductive Disorders.

Although IFNτ bears some similarity to the IFNα family based on structure and its potent antiviral properties, the IFNαs do not possess the reproductive properties associated with IFNτ. For example, recombinant human IFNα had no effect on interestrous interval compared to IFNτ, even when administered at twice the dose (Davis, et al., 1992).

Therefore, although IFNτ has some structural similarities to other interferons, it has very distinctive properties of its own: for example, the capability of significantly influencing the biochemical events of the estrous cycle.

The IFNτ compositions of the present invention can be used in methods of enhancing fertility and prolonging the life span of the corpus luteum in female mammals as generally described in Hansen, et al. (1991), herein incorporated by reference. According to the teachings herein, such methods of enhancing fertility include oral administration of IFNτ in a therapeutically-effective amount. Further, the compositions may be similarly employed to regulate growth and development of uterine and/or fetal-placental tissues. Compositions containing human IFNτ are particularly useful for treatment of humans, since potential antigenic responses are less likely using a same-species protein.

C. IFNτ as an Antiviral Treatment

The antiviral activity of IFNτ has broad therapeutic applications without the toxic effects that are usually associated with IFNαs. As described above, IFNτ exerts its therapeutic activity without adverse effects on the cells. The relative lack of cytotoxicity of IFNτ makes it extremely valuable as an in vivo therapeutic agent and sets IFNτ apart from most other known antiviral agents and all other known interferons.

Formulations containing IFNτ can be orally-administered to inhibit viral replication. Further, the compositions can be employed in methods for affecting the immune relationship between fetus and mother, for example, in preventing transmission of maternal viruses (e.g., HIV) to the developing fetus. Compositions containing a human interferon-τ are particularly useful for treatment of humans, since potential antigenic responses are less likely using a homologous protein.

Examples of specific viral diseases which may be treated by orally-administered IFNτ include, but are not limited to, hepatitis A, hepatitis B, hepatitis C, non-A, non-B, non-C hepatitis, Epstein-Barr viral infection, HIV infection, herpes virus (EB, CML, herpes simplex), papilloma, poxvirus, picorna virus, adeno virus, rhino virus, HTLV I, HTLV II, and human rotavirus.

D. IFNτ as an Antiproliferative Treatment

IFNτ exhibits potent anticellular proliferation activity. Accordingly, pharmaceutical compositions containing IFNτ, suitable for oral administration, can be used to inhibit cellular growth without the negative side effects associated with other interferons which are currently known. Such compositions or formulations can be used to inhibit, prevent, or slow tumor growth.

Examples of specific cell proliferation disorders which may be treated by orally-administered IFNτ include, but are not limited to, hairy cell leukemia, Kaposi's Sarcoma, chronic myelogenous leukemia, multiple myeloma, superficial bladder cancer, skin cancer (basal cell carcinoma and malignant melanoma), renal cell carcinoma, ovarian cancer, low grade lymphocytic and cutaneous T cell lymphoma, and glioma.

Furthermore, the development of certain tumors is mediated by estrogen. Experiments performed in support of the present invention indicate that IFNτ can suppress estrogen receptor numbers. Therefore, the IFNτ-containing compositions may be particularly useful in the treatment or prevention of estrogen-dependent tumors.

E. Veterinary Applications

In addition to the uses of the methods of the present invention detailed above, it will be appreciated that the methods may be applied to the treatment of a variety of immune system disorders suffered by domesticated and wild animals. For example, hypothyroidism in dogs typically results from a progressive destruction of the thyroid, which may be associated with Lymphocytic thyroiditis (Kemppainen and Clark, 1994). Lymphocytic thyroiditis, which resembles Hashimoto's thyroiditis in humans, is thought to be an autoimmune disorder. According to the guidance presented herein, hypothyroidism due to Lymphocytic thyroiditis in dogs may be treated with IFNτ as described above.

Another type of autoimmune disorder in dogs that may be alleviated by treatment with IFNτ is characterized by antinuclear antibody (ANA) positivity, pyrexia and seronegative arthritis (Day, et al., 1985). Immune-mediated thrombocytopenia (ITP; Kristensen, et al., 1994; Werner, et al., 1985), systemic lupus erythematosus (Kristensen, et al., 1994), and leukopenia and Coomb's positive hemolytic anemia (Werner, et al., 1985), may also be amenable to treatment using methods of the present invention.

V. IFN Pharmaceutical Composition Useful for Oral Administration

A. Formulation

Therapeutic preparations containing IFNτ or related polypeptides or proteins can be formulated according to known methods for preparing pharmaceutically useful compositions. Formulations comprising polypeptides like interferons have been previously described (e.g., Martin, 1976). In general, the IFNτ therapeutic compositions are formulated such that an effective amount of the IFNτ is combined with a suitable additive, carrier and/or excipient in order to facilitate effective oral administration of the composition. For example, tablets and capsules containing IFNτ may be prepared by combining IFNτ (e.g., lyophilized IFNτ protein) with additives such as pharmaceutically acceptable carriers (e.g., lactose, corn starch, light silicic anhydride, microcrystalline cellulose, sucrose), binders (e.g., alpha-form starch, methylcellulose, carboxymethylcellulose, hydroxypropylcellulose, hydroxypropylmethylcellulose, polyvinylpyrrolidone), disintegrating agents (e.g., carboxymethylcellulose calcium, starch, low substituted hydroxy-propylcellulose), surfactants (e.g., Tween 80, polyoxyethylene-polyoxypropylene copolymer), antioxidants (e.g., L-cysteine, sodium sulfite, sodium ascorbate), lubricants (e.g., magnesium stearate, talc), or the like.

Further, IFNτ polypeptides of the present invention can be mixed with a solid, pulverulent or other carrier, for example lactose, saccharose, sorbitol, mannitol, starch, such as potato starch, corn starch, millopectine, cellulose derivative or gelatine, and may also include lubricants, such as magnesium or calcium stearate, or polyethylene glycol waxes compressed to the formation of tablets. By using several layers of the carrier or diluent, tablets operating with slow release can be prepared.

Liquid preparations for oral administration can be made in the form of elixirs, syrups or suspensions, for example solutions containing from about 0.1 to about 30% by weight of IFNτ, sugar and a mixture of ethanol, water, glycerol, propylene, glycol and possibly other additives of a conventional nature.

B. Dosage

An orally-active IFNτ pharmaceutical composition is administered in a therapeutically-effective amount to an individual in need of treatment. The dose may vary considerably and is dependent on factors such as the seriousness of the disorder, the age and the weight of the patient, other medications that the patient may be taking and the like. This amount or dosage is typically determined by the attending physician. The dosage will typically be between about $1 \times 10^5$ and $1 \times 10^5$ units/day, preferably between about $1 \times 10^6$ and $1 \times 10^7$ units/day. It will be appreciated that because of its lower toxicity, IFNτ can be administered at higher doses than, for example, IFNβ. By way of comparison, patients with multiple sclerosis (MS) were treated with $10^6$ U and $8 \times 10^6$ U of IFNβ. Patients receiving $8 \times 10^6$ U suffered fewer relapses of disease than did patients receiving $10^6$ U. However, patients receiving the higher dose of IFNβ ($8 \times 10^6$ U) also exhibited more side-effects associated with IFNβ's toxicity. In view of the lower toxicity of IFNτ, these higher effective dosages could be administered without the associated toxic side-effects.

Disorders requiring a steady elevated level of IFNτ in plasma will benefit from administration as often as about every two to four hours, while other disorders, such as MS, may be effectively treated by administering a therapeutically-effective dose at less frequent intervals, e.g., once every 48 hours. The rate of administration of individual doses is typically adjusted by an attending physician to enable administration of the lowest total dosage while alleviating the severity of the disease being treated.

Once improvement of a patient's condition has occurred, a maintenance dose is administered if necessary. Subsequently, the dosage or the frequency of administration, or both, may be reduced, as a function of the symptoms, to a level at which the improved condition is retained.

C. Combination Therapies

It will, of course, be understood that the compositions and methods of this invention may be used in combination with other therapies. For example, in view of IFNτ's relative lack of toxicity at high dosages, MS patients that do not show improvement at IFNβ1b's low dosage or could not tolerate IFNβ1b due to toxicity may benefit from subsequent or simultaneous treatment with higher dosages of IFNτ or peptides derived therefrom. Further, development of neutralizing antibodies has been demonstrated in IFNβ1b treated patients (Weinstock-Guttman, et al., 1995). In cases where such neutralizing antibodies prove to impede the effectiveness of IFNβ1b, IFNτ may be an important alternative therapy, since antibody cross-reactivity is unlikely to occur, and IFNτ is unlikely to generate neutralizing antibodies (see Example 7). Orally-administered IFNτ is particularly advantageous in this respect, since it causes a significantly lower anti-IFNτ antibody response than injected IFNτ.

Another type of combination therapy enabled by the present invention is the oral administration of an antigen against which an autoimmune response is directed in combination with IFNτ. Oral administration of such an antigen can result in tolerization, reducing the severity of the autoimmune disease (for review, see, e.g., Weiner, et al., 1994). It is contemplated that the IFNτ has a synergistic effect with the tolerization induced by the antigen, thereby alleviating the severity of the autoimmune disease. For example, MBP has been shown to suppress EAE (Lider, et al., 1989). According to the methods of the present invention, MBP may be administered in combination with IFNτ to treat multiple sclerosis. Other examples include administration of IFNτ with collagen to treat rheumatoid arthritis, and with acetylcholine receptor polypeptides to treat myasthenia gravis.

Furthermore, IFNτ may be orally administered with known immunosuppressants, such as steroids, to treat autoimmune diseases such a multiple sclerosis. The immunosuppressants may act synergistically with IFNτ and result in a more effective treatment that could be obtained with an equivalent dose of IFNτ or the immunosuppressant alone.

Similarly, in a treatment for a cancer or viral disease, IFNτ may be administered in conjunction with, e.g., a therapeutically effective amount of one or more chemotherapy agents such as busulfan, 5-fluoro-uracil (5--FU), zidovudine (AZT), leucovorin, melphalan, prednisone, cyclophosphamide, dacarbazine, cisplatin, and dipyridamole.

The following examples illustrate but in no way are intended to limit the present invention.

VI. MATERIALS AND METHODS

A. Buffers

Phosphate-buffered saline (PBS)
10×stock solution, 1 liter:
80 g NaCl
2 g KCl
11.5 g $Na_2HPO4-7H_2O$
2 g $KH_2 PO_4$ Working solution, pH 7.3:
137 mM NaCl
2.7 mM KCl
4.3 mM $Na_2HPO_4$-$7H_2O$
1.4 mM $KH_2PO_4$

B. General ELISA Protocol for Detection of Antibodies

Polystyrene 96 well plates Immulon II (PGC) were coated with 5 μg/mL (100 μL per well) antigen in 0.1 M carbonate/bicarbonate buffer, pH 9.5. The plates were sealed with parafilm and stored at 4° C. overnight.

Following incubation, the plates were aspirated and blocked with 300 μL 10% NGS and incubated at 37° C. for 1 hr. The plates were then washed 5 times with PBS 0.5% "TWEEN-20". Antisera were diluted in 0.1 M PBS, pH 7.2. The desired dilution(s) of antisera (0.1 mL) were added to each well and the plates incubated 1 hour at 37° C. The plates were then washed 5 times with PBS 0.5% "TWEEN-20".

Horseradish peroxidase (HRP) conjugated goat anti-human antiserum (Cappel, Durham, N.C.) was diluted 1/5,000 in PBS. 0.1 mL of this solution was added to each well. The plate was incubated 30 min at 37° C., then washed 5 times with PBS.

Sigma ABTS (substrate) was prepared just prior to addition to the plate. The reagent consists of 50 mL 0.05 M citric acid, pH 4.2, 0.078 mL 30% hydrogen peroxide solution and 15 mg ABTS. 0.1 mL of the substrate was added to each well, then incubated for 30 min at room temperature. The reaction was stopped with the addition of 0.050 mL 5% SDS (w/v). The relative absorbance is determined at 410 nm.

C. Production of OvIFN-τ

A synthetic OvIFNτ gene was generated using standard molecular methods (Ausubel, et al., 1988) by ligating oligonucloetides containing contiguous portions of a DNA sequence encoding the OvIFNτ amino acid sequence (Imakawa, et al., 1987). The resulting IFNτ polynucleotide coding sequence spans position 16 through 531: a coding sequence of 172 amino acids.

The full length synthetic gene StuI/SstI fragment (540 bp) was cloned into a modified pIN III omp-A expression vector and transformed into a competent SB221 strain of E. coli. For expression of the IFNτ protein, cells carrying the expression vector were grown in L-broth containing ampicillin to an OD (550 nm) of 0.1–1, induced with IPTG (isopropyl-1-thio-b-D-galactoside) for 3 hours and harvested by centrifugation. Soluble recombinant IFNτ was liberated from the cells by sonication or osmotic fractionation.

For expression in yeast, the IFNτ gene was amplified using polymerase chain reaction (PCR; Mullis, 1987; Mullis, et al., 1987) with PCR primers containing StuI and SacI restriction sites at the 5' and 3' ends, respectively. The amplified fragments were digested with StuI and SacII and ligated into the SacII and SmaI sites of "pBLUESCRIPT+ (KS)", generating pBSY-IFNτ.

Plasmid pBSY-IFNτ was digested with SacII and EcoRV and the fragment containing the synthetic IFNτ gene was isolated. The yeast expression vector pBS24Ub (Sabin, et al., 1989; Ecker, et al., 1989) was digested with SalI. Blunt ends were generated using T4 DNA polymerase. The vector DNA was extracted with phenol and ethanol precipitated (Sambrook, et al., 1989). The recovered plasmid was digested with SacII, purified by agarose gel electrophoresis, and ligated to the SacII-EcoRV fragment isolated from pBSY-IFNτ. The resulting recombinant plasmid was designated pBS24Ub-IFNτ.

The recombinant plasmid pBS24Ub-IFNτ was transformed into E. coli. Recombinant clones containing the IFNτ insert were isolated and identified by restriction enzyme analysis. IFNτ coding sequences were isolated form pBS24Ub-IFNτ and cloned into a Pichia pastoris expression vector containing the alcohol oxidase (AOX1) promoter (Invitrogen, San Diego, Calif.). The vector was then used to transform Pichia pastoris GS115 His⁻ host cells and protein was expressed following the manufacturer's instructions. The protein was secreted into the medium and purified by successive DEAE-cellulose and hydroxyapatite chromatography to electrophoretic homogeneity as determined by SDS-PAGE and silver staining. The purified protein had a specific activity of about 0.29 to about 0.4433 $10^8$ U/mg as measured by anti-viral activity on Madin-Darby bovine kidney (MDBK) cells.

EXAMPLE 1

Orally-Administered OvIFNτ Blocks Development of Experimental Allergic Encephalomyelitis Orally-administered and injected IFN-τ was tested for its ability to prevent the induction of EAE. Recipient New Zealand White (NZW) mice received OvIFNτ ($10^5$ U/ml) by either i.p. injection or oral feeding 48 hours prior to, on the day of, and 48 hours after immunization with bovine myelin basic protein (bMBP) for induction of experimental allergic encephalomyelitis (EAE). $10^5$ U of IFNτ were mixed with PBS to a total volume of 100 μl and administered using a feeding tube placed down the esophagus and into the stomach. The dilution of the IFNτ in PBS was done immediately before administration.

For induction of EAE in NZW mice, 300 μg of bovine myelin basic protein (bMBP) was emulsified in complete Freund's adjuvant (CFA) containing 8 mg/ml of H37Ra (Mycobacterium tuberculosis, Difco, Detroit, Mich.) and injected on either side of the base of the tail. On the day of immunization and 48 hours later, 400 ng of Pertussis toxin (List Biologicals, Campbell, Calif.) was also injected. For induction of EAE in SJL/J mice, the same protocol was used as described except mice were immunized again 7 days after the initial immunization. Mice were examined daily for signs of EAE and severity of disease was graded on the following scale: 1, loss of tail tone; 2, hind limb weakness; 3, paraparesis; 4, paraplegia; 5, moribund/death.

To determine whether prevention of EAE was specific to OvIFNτ treatment, an anti-OvIFNτ monoclonal antibody (mAb), HL127, was used to neutralize OvIFNτ ability to block EAE (antibody HL127, directed against aa 139-172 of SEQ ID NO:2, neutralizes the antiviral activity of OvIFNτ in an antiviral assay using the MDBK cell line). A 1:10 dilution of HL127 was incubated for 2 hours with OvIFNτ prior to administration by either i.p. injection or oral feeding. Antibodies directed against IFNτ antigens, may be generated using the information herein combined with known techniques for antibody production (e.g., Harlow, et al., 1988).

The results are shown in Table 3, below. Both oral feeding and i.p. injection of OvIFNτ protected against acute induction of EAE. None of the animals that received IFNτ via i.p. injection developed symptoms of EAE, while of the animals that received IFNτ orally, 7 of 9 (78%) were protected. Anti-OvIFNτ antibody HL127 was effective at partially neutralizing the ability of the OvIFNτ to block EAE. These data indicate that orally-administered IFNτ is effective as a treatment in an animal model of multiple sclerosis.

TABLE 3

Oral Feeding of OvIFNτ Blocks Acute
EAE and Can Be Reversed by an OvIFNτ
Specific Monoclonal Antibody in NZW Mice

| ROUTE OF ADMINISTRATION | TREATMENT | DISEASE INCIDENCE | MEAN DAY OF ONSET | MEAN SEVERITY |
|---|---|---|---|---|
| i.p. | PBS | 4/4 | 24.8 ± 2.1 | 2.5 ± 0 |
| i.p. | OvIFNτ | 0/4 | — | — |
| i.p. | OvIFNτ ± HL127 | 3/4 | 20.7 ± 1.2 | 2.3 ± 0.6 |
| oral | PBS | 7/9 | 22.0 ± 1.0 | 2.7 ± 0.6 |
| oral | OvIFNτ | 2/9 | 19 | 3 |
| oral | OvIFNτ ± HL127 | 5/8 | 20.7 ± 0.6 | 3 ± 0 |

OvIFNτ ($10^5$ U) was administered 48 hours prior to MBP immunization, on the day of MBP immunization and 48 hours after MBP immunization by either i.p. injection or oral feeding. HL127, a monoclonal antibody specific for OvIFNτ, was incubated with OvIFNτ for two hours prior to administration.

EXAMPLE 2

Detection of OvIFNτ in Sera following Oral Administration

The amount of OvIFNτ detectable in the sera of mice (treated as above) was compared over time after oral feeding or i.p. injection of OvIFNτ. Mice were administered $3 \times 10^5$ U of OvIFNτ and bled at 0.5, 2, 4, 6, 24 and 48 hours following IFNτ administration. Sera were tested in a cytopathic effect (viral plaque) assay (Familetti, et al., 1981) to determine the amount of IFNτ in the samples.

Briefly, dilutions of IFNτ were added to MDBK cells grown to confluency in a flat bottom 96 well plate and incubated for 18 to 24 hours at 37° C. Vesicular stomatatosis virus (VSV) was added to the plate for 45 minutes at room temperature. Virus was removed and methyl cellulose was added and the plate incubated for 48 hours at 37° C. After removal of methyl cellulose, the plate was stained with crystal violet for visualization of plaques. For measurement of IFN neutralization, OvIFNτ at a concentration of 500 U/ml was incubated for 1 hour at 37° C. with either sera or HL127 (a monoclonal specific of OvIFNτ). One antiviral unit caused a 50% reduction in destruction of the monolayer, relative to untreated MDBK cells infected with VSV (control plates). All samples were assayed simultaneously to eliminate interassay variability.

As shown in FIG. 1, OvIFNτ was detected at 0.5 hour and 2 hours after oral feeding (filled bars) at levels of 200 U/ml. By comparison, somewhat higher levels of OvIFNτ were detected for over a 24 hour period of time after i.p. injection (open bars). These data show that the above dose of IFNτ can be detected in serum for about two hours following oral administration.

EXAMPLE 3

Prevention of Chronic Relapse of Experimental Allergic Encephalomyelitis by Orally-Administered OvIFNτ

The ability of OvIFNτ to prevent paralysis was examined using a chronic-relapsing model of EAE, in which SJL mice immunized with MBP develop a chronic form of the disease where the appearance of symptoms occurs in a relapsing-remitting manner (Zamvil and Steinman, 1990).

EAE was induced in SJL mice essentially as described above. The mice were treated with $10^5$ U of OvIFNτ by either i.p. injection or oral feeding on the day of immunization (day 0) and every 48 hours thereafter for the duration of the experiment. As presented in FIG. 2A, SJL mice which were immunized with MBP but did not receive OvIFNτ treatment developed chronic relapsing paralysis with a 5/5 incidence of disease, with a peak mean severity of ~2.5 occurring 14 days after the start of the experiment. In contrast, treatment with OvIFNτ by either i.p. injection or oral feeding (FIGS. 2B and 2C, respectively) resulted in protection from EAE. Incidence of disease in both OvIFNτ treatment groups was reduced to 1/5 animals, with a mean severity of ~1.0. These data indicate that oral administration of IFNτ can block the development of chronic relapsing EAE, and suggest that orally-administered IFNτ may be as effective as i.p. injection when the IFNτ is fed about every 48 hours over an extended period of time.

EXAMPLE 4

Histological Analysis

Histological analyses were performed to determine the extent of lymphocyte infiltration into the CNS of MBP-immunized mice treated with OvIFNτ by oral and i.p. routes.

Mice were perfused with 4% paraformaldehyde, vertebral columns were removed and treated with formalin for 2 to 3 days. Spinal cords were dissected out and soaked in 0.5% sucrose overnight at 4° C. Spinal cord sections were embedded and sections cut in a microtome. Sections were fixed to slides in 4% paraformaldehyde and stained with cresyl violet for visualization of inflammatory infiltrates.

Figure 3A:
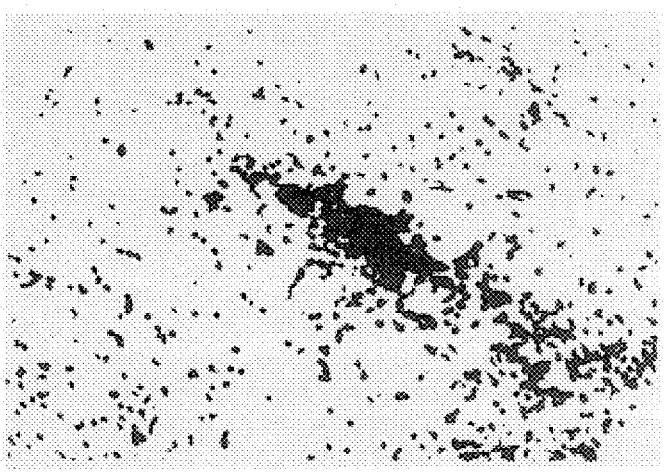
FIGS. 3A, 3B and 3C show sections of mouse spinal cord stained with cresyl violet for detection of lymphocyte infiltration from EAE-induced animals receiving either no IFNτ treatment (FIG. 3A), OvIFNτ treatment by i.p. injection (FIG. 3B) or OvIFNτ treatment by oral feeding (FIG. 3C).
Figure 3B:
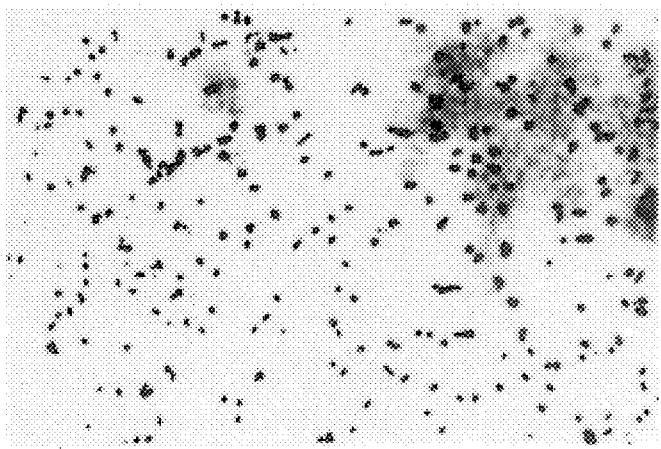
Figure 3C:
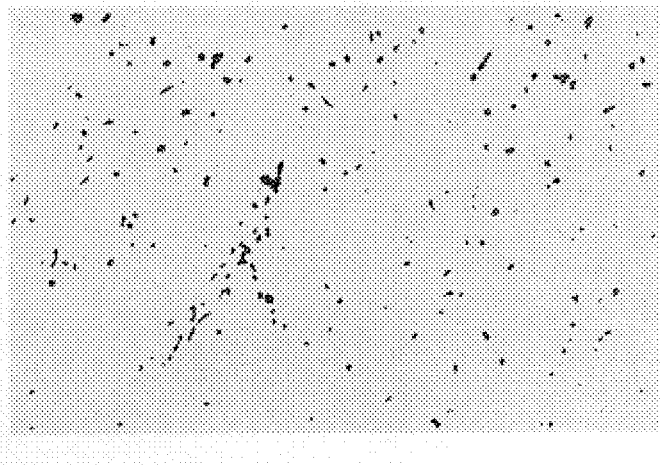

The results are shown in FIGS. 3A, 3B and 3C at a final magnification of 222×. Lymphocytic lesions were present in control spinal cord white matter (FIG. 3A). In contrast, no lymphocytic infiltrates were detected in mice treated with OvIFNτ by i.p. injection (FIG. 3B) or oral feeding (FIG. 3C). These data suggest that the protective effect of IFNτ is associated with inhibition of lymphocyte infiltration of the CNS.

EXAMPLE 5

Induction of IL10 by Treatment with OvIFNτ

During the course of OvIFNτ treatment of SJL for prevention of chronic relapsing EAE, mice were bled and sera were examined for the presence of interleukin 10 (IL10). Sera from mice which received either a single IFNτ ($10^5$ U) treatment (by i.p. injection or oral feeding), prolonged IFNτ ($10^5$ U) treatment (by i.p. injection or oral treatment for greater than 20 days) or no treatment were examined for IL10 by enzyme-linked immunosorbent assay (ELISA) using IL10 ELISA kits (Genzyme, Cambridge, Mass.) following the manufacturer's instructions. All sera samples were tested in duplicate.

Figure 4:
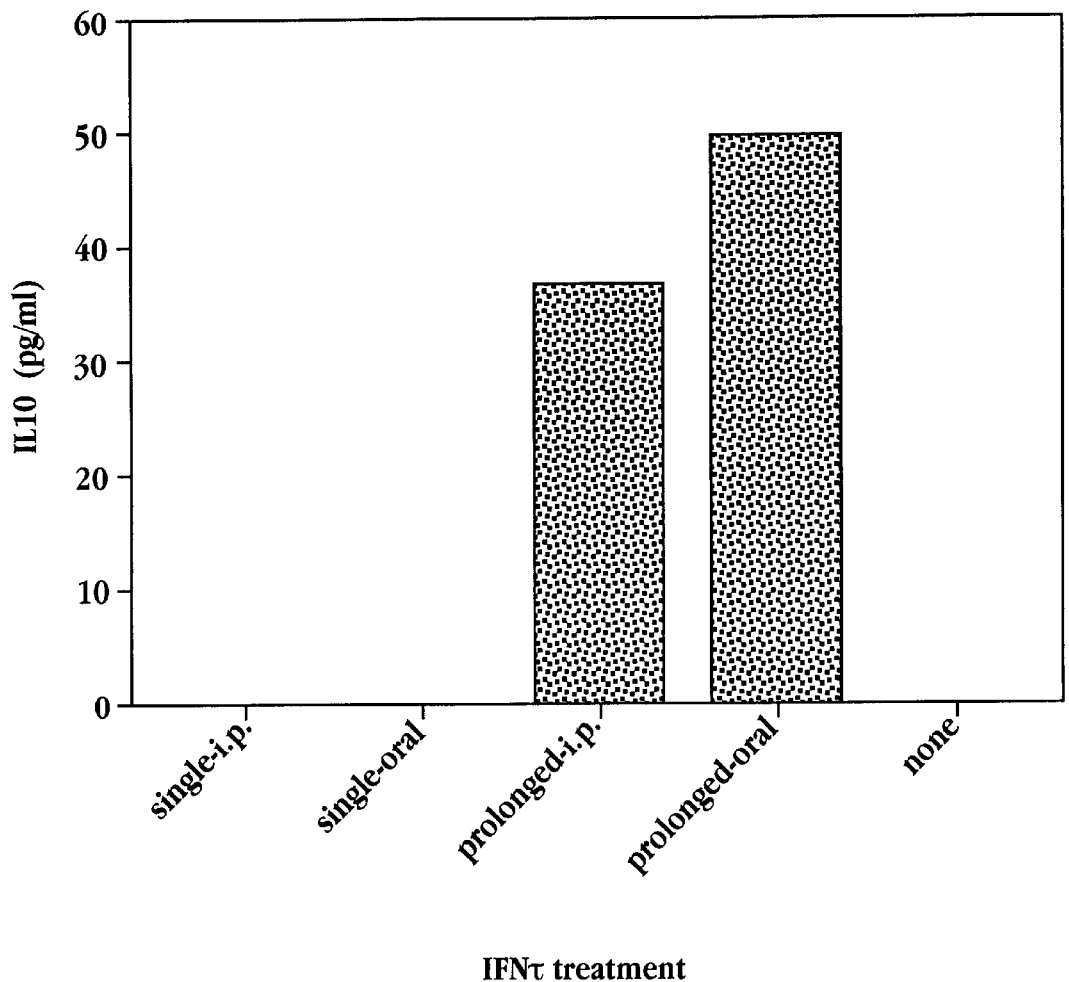
FIG. 4 shows induction of IL-10 by either single-dose or prolonged IFNτ treatment administered by i.p. injection or oral feeding.

No IL10 was detected in control mice or in mice which received a single treatment of OvIFNτ by either i.p. injection or oral feeding. In contrast, SJL mice which received OvIFNτ by either i.p. injection or oral feeding every 48 hours for greater than 20 days had detectable levels of IL10 in their sera (FIG. 4). These data suggest that IFNτ-induced production of IL10 may be a contributing mechanism by which OvIFNτ prevents development of EAE.

EXAMPLE 6

Cessation of Treatment with OvIFNτ Results in Relapsing Paralysis

SJL mice which were protected from EAE by OvIFNτ treatment via i.p. injection or oral feeding (every 48 hours) were followed for 58 days, during which time no disease development was observed. Treatment with OvIFNτ was then removed and the mice were observed for an additional 22 days for symptoms of disease.

The results are shown in FIG. 5. IFNτ treatment is denoted as plus signs and removal of IFNτ treatment is denoted as minus signs beneath the graph. Disease incidence in each treatment group was as follows: PBS control=3/4 (square); i.p. injection=3/3 (triangle); oral feeding=:3/4 (circle).

Both groups of mice which had previously been protected from EAE by OvIFNτ treatment developed signs of paralysis 6 to 12 days after removal of the OvIFNτ treatment. These data indicate that ongoing administration of IFNτ, by either i.p. injection or oral feeding, is desirable for continued protection from EAE in the chronic-relapsing model of EAE.

EXAMPLE 7

Oral Administration of OvIFNτ Reduces Anti-OvIFNτ Antibody Response

After removal of OvIFNτ treatment in the experiments described in Example 6, above, mice from each treatment group were bled and sera were examined for the presence of anti-OvIFNτ antibodies (Ab).

The antigen, OvIFNτ, was adsorbed to the flat bottoms of plastic tissue culture wells overnight at a concentration of 600 ng/well, and subsequently evaporated to dryness. The plates were treated with 5% milk (Carnation) in PBS for 2 hours in order to block nonspecific binding and then washed 3 times with PBS containing 0.05% Tween 20. Various dilutions of sera from mice which were untreated, OvIFNτ treated by i.p. injection and OvIFNτ treated by oral feeding were added and incubated for 3 hours. Binding was assessed with goat anti-mouse immunoglobulin coupled to horseradish peroxidase. Color development was monitored at 492 nm in an ELISA plate reader (Bio-Rad, Richmond, Calif.) after o-phenylenediamine and $H_2O_2$ were added and the reaction terminated with 2M $H_2SO_4$.

Figure 6:
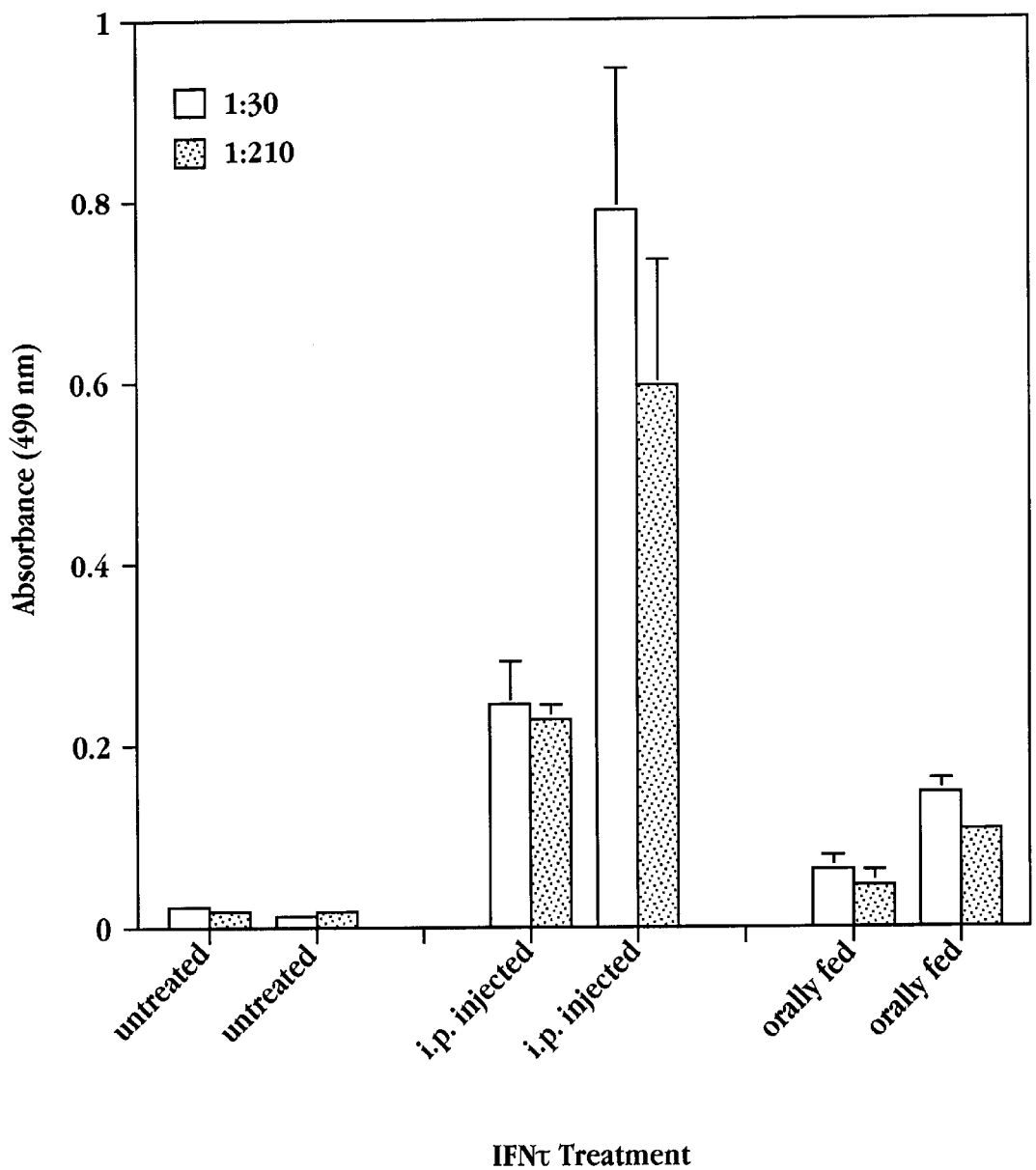
FIG. 6 shows ELISA detection of anti-OvIFNτ antibodies in the sera of OvIFNτ-treated mice following i.p. injection or oral feeding of OvIFNτ.

Exemplary results are shown in FIG. 6. Sera from untreated, OvIFNτ treated-i.p. injected and OvIFNτ treated-orally fed (2 mice/group) were examined by ELISA using multiple dilutions, including 1:30 (open bars) and 1:120 (filled bars). Mice which received OvIFNτ by oral feeding exhibited minimal Ab levels while mice which received OvIFNτ by i.p. injection exhibited elevated levels of anti-OvIFNτ Ab. As expected, mice which received no OvIFNτ treatment displayed no anti-OvIFNτ Ab.

Sera were also examined for their ability to neutralize OvIFNτ antiviral activity on MDBK cells as described above. The results are shown in Table 4, below. None of the sera from either i.p. injected or orally fed mice possessed neutralizing activity. These data suggest that oral treatment with IFNτ circumvents the Ab response directed against OvIFNτ protein observed in i.p. injection-treated individuals, and that neither treatment typically results in the generation of neutralizing antibodies.

TABLE 4

Sera from Mice Treated with OvIFNτ by i.p. Injection or Oral Feeding do Not Possess Neutralizing Activity

| 500 U/ML of OvIFNτ COCULTURED WITH SERA FROM: | OvIFNτ TITER (U/ML) |
|---|---|
| untreated | 500 |
| i.p. injected | 500 |
| orally fed | 500 |
| HL127 | <50 |

While the invention has been described with reference to specific methods and embodiments, it is appreciated that various modifications and changes may be made without departing from the invention.

It is claimed:

1. In a method of treating a viral disease in a mammal responsive to treatment by ovine or human interferon-tau (IFN$_\tau$), an improvement comprising orally administering a therapeutically-effective amount of IFN$_\tau$ through oral ingestion.

2. The method of claim 1, wherein IFN$_\tau$ is orally-administered at a dosage of greater than about $1 \times 10^5$ units per day.

3. The method of claim 1, wherein IFN$_\tau$ is orally-administered at a dosage of greater than about $1 \times 10^6$ units per day.

4. The method of claim 1, wherein the orally-administered IFNτ is ovine IFNτ (OvIFNτ).

5. The method of claim 4, wherein said OvIFN$_\tau$ has the sequence represented as SEQ ID NO:2.

6. The method of claim 1, wherein the orally-administered IFNτ is human IFNτ (HuIFNτ).

7. The method of claim 6, wherein said HuIFN$_\tau$ has the sequence represented as SEQ ID NO:4.

8. The method of claim 1, wherein said mammal is a human.

9. The method of claim 1, wherein said mammal is a dog.

10. The method of claim 1, wherein the mammal is a domesticated animal.

11. The method of claim 1, wherein said IFN$_\tau$ has an amino acid sequence that is at least about 80% homologous with ovine IFN$_\tau$.

12. In a method of treating a condition associated with cellular proliferation in a mammal responsive to treatment by ovine or human interferon-tau (IFN$_\tau$), an improvement comprising orally administering a therapeutically-effective amount of IFN$_\tau$ through oral ingestion.

13. The method of claim 12, wherein IFN$_\tau$ is orally-administered at a dosage of greater than about $1 \times 10^5$ units per day.

14. The method of claim 12, wherein IFN$_\tau$ is orally-administered at a dosage of greater than about $1 \times 10^6$ units per day.

15. The method of claim 12, wherein the orally-administered IFN$_\tau$ is ovine IFN$_\tau$ (OvIFN$_\tau$).

16. The method of claim 15, wherein said OvIFN$_\tau$ has the sequence represented as SEQ ID NO:2.

17. The method of claim 12, wherein said IFN$_\tau$ has an amino acid sequence that is at least about 80% homologous to ovine IFN$_\tau$.

18. The method of claim 12, wherein the orally-administered IFN$_\tau$ is human IFN$_\tau$ (HuIFN$_\tau$).

19. The method of claim 18, wherein said HuIFN$_\tau$ has the sequence represented as SEQ ID NO:4.

20. The method of claim 12, wherein said mammal is a human.

21. The method of claim 12, wherein the mammal is a domesticated animal.

22. The method of claim 21, wherein said mammal is a dog.

23. In a method of treating an inflammatory disease condition in a mammal responsive to treatment by ovine or human interferon-tau (IFN$_\tau$), an improvement comprising orally administering a therapeutically-effective amount of IFN$_\tau$ through oral ingestion.

24. The method of claim 23, wherein IFN$_\tau$ is orally-administered at a dosage of greater than about $1 \times 10^5$ units per day.

25. The method of claim 23, wherein IFN$_\tau$ is orally-administered at a dosage of greater than about $1 \times 10^6$ units per day.

26. The method of claim 23, wherein the orally-administered IFN$_\tau$ is ovine IFN$_\tau$ (OvIFN$_\tau$).

27. The method of claim 26, wherein said OvIFN$_\tau$ has the sequence represented as SEQ ID NO:2.

28. The method of claim 23, wherein said IFN$_\tau$ has an amino acid sequence that is at least about 80% homologous to ovine IFN$_\tau$.

29. The method of claim 23, wherein the orally-administered IFN$_\tau$ is human IFN$_\tau$ (HuIFN$_\tau$).

30. The method of claim 29, wherein said HuIFN$_\tau$ has the sequence represented as SEQ ID NO:4.

31. The method of claim 23, wherein said mammal is a human.

32. The method of claim 23, wherein the mammal is a domesticated animal.

33. The method of claim 32, wherein said mammal is a dog.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 516 base pairs
      (B) TYPE: nucleic acid
      (C) STRANDEDNESS: double
      (D) TOPOLOGY: circular (ii) MOLECULE TYPE: DNA

```
    (iii) HYPOTHETICAL: NO (iv) ANTI-SENSE: NO (vi) ORIGINAL SOURCE:
         (A) ORGANISM: Ovis aries
         (B) STRAIN: Domestic
         (D) DEVELOPMENTAL STAGE: Blastula (blastocyst)
         (F) TISSUE TYPE: Trophectoderm
         (G) CELL TYPE: Mononuclear trophectoderm cells (vii) IMMEDIATE SOURCE:
         (B) CLONE: oTP-1a (viii) POSITION IN GENOME:
         (C) UNITS: bp (ix) FEATURE:
         (A) NAME/KEY: CDS
         (B) LOCATION: 1..516

(x) PUBLICATION INFORMATION:
         (A) AUTHORS: Ott, Troy L
                     Van Heeke, Gino
                     Johnson, Howard M
                     Bazer, Fuller W
         (B) TITLE: Cloning and Expression in Saccharomyces
                    cerevisiae of a Synthetic Gene for the Type I
                    Trophoblast Interferon Ovine Trophoblast
                    Protein-1:Purification and Antiviral Activity
         (C) JOURNAL: J. Interferon Res.
         (D) VOLUME: 11
         (F) PAGES: 357-364
         (G) DATE: 1991
         (K) RELEVANT RESIDUES IN SEQ ID NO:1: FROM 1 TO 516

(xi) SEQUENCE DESCRIPTION: SEQ ID NO:1:

TGC TAC CTG TCG CGA AAA CTG ATG CTG GAC GCT CGA GAA AAT TTA AAA        48
Cys Tyr Leu Ser Arg Lys Leu Met Leu Asp Ala Arg Glu Asn Leu Lys
  1               5                  10                  15

CTG CTG GAC CGT ATG AAT CGA TTG TCT CCG CAC AGC TGC CTG CAA GAC        96
Leu Leu Asp Arg Met Asn Arg Leu Ser Pro His Ser Cys Leu Gln Asp
             20                  25                  30

CGG AAA GAC TTC GGT CTG CCG CAG GAA ATG GTT GAA GGT GAC CAA CTG       144
Arg Lys Asp Phe Gly Leu Pro Gln Glu Met Val Glu Gly Asp Gln Leu
         35                  40                  45

CAA AAA GAC CAA GCT TTC CCG GTA CTG TAT GAA ATG CTG CAG CAG TCT       192
Gln Lys Asp Gln Ala Phe Pro Val Leu Tyr Glu Met Leu Gln Gln Ser
     50                  55                  60

TTC AAC CTG TTC TAC ACT GAA CAT TCT TCG GCC GCT TGG GAC ACT ACT       240
Phe Asn Leu Phe Tyr Thr Glu His Ser Ser Ala Ala Trp Asp Thr Thr
 65                  70                  75                  80

CTT CTA GAA CAA CTG TGC ACT GGT CTG CAA CAG CAA CTG GAC CAT CTG       288
Leu Leu Glu Gln Leu Cys Thr Gly Leu Gln Gln Gln Leu Asp His Leu
                 85                  90                  95

GAC ACT TGC CGT GGC CAG GTT ATG GGT GAA GAA GAC TCT GAA CTG GGT       336
Asp Thr Cys Arg Gly Gln Val Met Gly Glu Glu Asp Ser Glu Leu Gly
            100                 105                 110

AAC ATG GAT CCG ATC GTT ACT GTT AAA AAA TAT TTC CAG GGT ATC TAC       384
Asn Met Asp Pro Ile Val Thr Val Lys Lys Tyr Phe Gln Gly Ile Tyr
        115                 120                 125

GAC TAC CTG CAG GAA AAA GGT TAC TCT GAC TGC GCT TGG GAA ATC GTA       432
Asp Tyr Leu Gln Glu Lys Gly Tyr Ser Asp Cys Ala Trp Glu Ile Val
    130                 135                 140

CGC GTT GAA ATG ATG CGG GCC CTG ACT GTG TCG ACT ACT CTG CAA AAA       480
Arg Val Glu Met Met Arg Ala Leu Thr Val Ser Thr Thr Leu Gln Lys
145                 150                 155                 160
```

```
CGG TTA ACT AAA ATG GGT GGT GAC CTG AAT TCT CCG              516
Arg Leu Thr Lys Met Gly Gly Asp Leu Asn Ser Pro
            165                 170
```

(2) INFORMATION FOR SEQ ID NO:2:

(i) SEQUENCE CHARACTERISTICS:
        (A) LENGTH: 172 amino acids
        (B) TYPE: amino acid
        (D) TOPOLOGY: linear (ii) MOLECULE TYPE: protein (vi) ORIGINAL SOURCE:
        (C) INDIVIDUAL ISOLATE: amino acid sequence of a mature
           OvIFNtau protein (xi) SEQUENCE DESCRIPTION: SEQ ID NO:2:

```
Cys Tyr Leu Ser Arg Lys Leu Met Leu Asp Ala Arg Glu Asn Leu Lys
 1               5                  10                  15

Leu Leu Asp Arg Met Asn Arg Leu Ser Pro His Ser Cys Leu Gln Asp
            20                  25                  30

Arg Lys Asp Phe Gly Leu Pro Gln Glu Met Val Glu Gly Asp Gln Leu
        35                  40                  45

Gln Lys Asp Gln Ala Phe Pro Val Leu Tyr Glu Met Leu Gln Gln Ser
    50                  55                  60

Phe Asn Leu Phe Tyr Thr Glu His Ser Ser Ala Ala Trp Asp Thr Thr
65                  70                  75                  80

Leu Leu Glu Gln Leu Cys Thr Gly Leu Gln Gln Gln Leu Asp His Leu
                85                  90                  95

Asp Thr Cys Arg Gly Gln Val Met Gly Glu Glu Asp Ser Glu Leu Gly
            100                 105                 110

Asn Met Asp Pro Ile Val Thr Val Lys Lys Tyr Phe Gln Gly Ile Tyr
        115                 120                 125

Asp Tyr Leu Gln Glu Lys Gly Tyr Ser Asp Cys Ala Trp Glu Ile Val
    130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
            165                 170
```

(2) INFORMATION FOR SEQ ID NO:3:

(i) SEQUENCE CHARACTERISTICS:
        (A) LENGTH: 516 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (C) INDIVIDUAL ISOLATE: synthetic nucleotide sequence encoding
           a mature human interferon-tau protein, HuIFNtau1.

(xi) SEQUENCE DESCRIPTION: SEQ ID NO:3:

```
TGTGACTTGT CTCAAAACCA CGTTTTGGTT GGTAGAAAGA ACTTAAGACT ACTAGACGAA    60

ATGAGACGTC TATCTCCACG CTTCTGTCTA CAAGACAGAA AGGACTTCGC TTTGCCTCAG   120

GAAATGGTTG AAGGTGGCCA ACTACAAGAA GCTCAAGCGA TATCTGTTTT GCACGAAATG   180

TTGCAACAAA GCTTCAACTT GTTCCACACC GAACACTCTT CGGCCGCTTG GGACACCACC   240

TTGTTGGAAC AGCTCAGAAC CGGTTTGCAC CAACAATTGG ACAACTTGGA TGCATGTTTG   300
```

```
GGTCAAGTTA TGGGTGAAGA AGACTCTGCT CTCGGGAGAA CCGGTCCAAC GCTAGCTTTG    360

AAGAGATACT TCCAAGGTAT CCACGTTTAC TTGAAGGAAA AGGGTTACTC TGACTGTGCT    420

TGGGAAACCG TGCGTCTAGA AATCATGCGT AGCTTCTCTT CTTTGATCAG CTTGCAAGAA    480

AGATTACGTA TGATGGACGG TGACTTGTCG AGCCCA                              516
```

(2) INFORMATION FOR SEQ ID NO:4:

(i) SEQUENCE CHARACTERISTICS:
        (A) LENGTH: 172 amino acids
        (B) TYPE: amino acid
        (C) STRANDEDNESS: single
        (D) TOPOLOGY: linear (ii) MOLECULE TYPE: protein (vi) ORIGINAL SOURCE:
        (C) INDIVIDUAL ISOLATE: amino acid sequence for a mature
            HuIFNtau protein, HuIFNtau1.

(xi) SEQUENCE DESCRIPTION: SEQ ID NO:4:

```
Cys Asp Leu Ser Gln Asn His Val Leu Val Gly Arg Lys Asn Leu Arg
  1               5                  10                  15

Leu Leu Asp Glu Met Arg Arg Leu Ser Pro Arg Phe Cys Leu Gln Asp
             20                  25                  30

Arg Lys Asp Phe Ala Leu Pro Gln Glu Met Val Glu Gly Gly Gln Leu
         35                  40                  45

Gln Glu Ala Gln Ala Ile Ser Val Leu His Glu Met Leu Gln Gln Ser
     50                  55                  60

Phe Asn Leu Phe His Thr Glu His Ser Ser Ala Ala Trp Asp Thr Thr
 65                  70                  75                  80

Leu Leu Glu Gln Leu Arg Thr Gly Leu His Gln Gln Leu Asp Asn Leu
                 85                  90                  95

Asp Ala Cys Leu Gly Gln Val Met Gly Glu Glu Asp Ser Ala Leu Gly
            100                 105                 110

Arg Thr Gly Pro Thr Leu Ala Leu Lys Arg Tyr Phe Gln Gly Ile His
        115                 120                 125

Val Tyr Leu Lys Glu Lys Gly Tyr Ser Asp Cys Ala Trp Glu Thr Val
    130                 135                 140

Arg Leu Glu Ile Met Arg Ser Phe Ser Ser Leu Ile Ser Leu Gln Glu
145                 150                 155                 160

Arg Leu Arg Met Met Asp Gly Asp Leu Ser Ser Pro
                165                 170
```

(2) INFORMATION FOR SEQ ID NO:5:

(i) SEQUENCE CHARACTERISTICS:
        (A) LENGTH: 516 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: HuIFNtau3, mature no leader sequence (ix) FEATURE:
        (A) NAME/KEY: CDS (B) LOCATION: 1..516

(xi) SEQUENCE DESCRIPTION: SEQ ID NO:5:

```
TGT GAC CTG TCT CAG AAC CAC GTG CTG GTT GGC AGC CAG AAC CTC AGG      48
Cys Asp Leu Ser Gln Asn His Val Leu Val Gly Ser Gln Asn Leu Arg
 1               5                  10                  15

CTC CTG GGC CAA ATG AGG AGA CTC TCC CTT CGC TTC TGT CTG CAG GAC      96
Leu Leu Gly Gln Met Arg Arg Leu Ser Leu Arg Phe Cys Leu Gln Asp
            20                  25                  30

AGA AAA GAC TTC GCT TTC CCC CAG GAG ATG GTG GAG GGT GGC CAG CTC     144
Arg Lys Asp Phe Ala Phe Pro Gln Glu Met Val Glu Gly Gly Gln Leu
        35                  40                  45

CAG GAG GCC CAG GCC ATC TCT GTG CTC CAC GAG ATG CTC CAG CAG AGC     192
Gln Glu Ala Gln Ala Ile Ser Val Leu His Glu Met Leu Gln Gln Ser
50                  55                  60

TTC AAC CTC TTC CAC ACA GAG CAC TCC TCT GCT GCC TGG GAC ACC ACC     240
Phe Asn Leu Phe His Thr Glu His Ser Ser Ala Ala Trp Asp Thr Thr
65                  70                  75                  80

CTC CTG GAG CAG CTC CGC ACT GGA CTC CAT CAG CAG CTG GAT GAC CTG     288
Leu Leu Glu Gln Leu Arg Thr Gly Leu His Gln Gln Leu Asp Asp Leu
                85                  90                  95

GAT GCC TGC CTG GGG CAG GTG ACG GGA GAG GAA GAC TCT GCC CTG GGA     336
Asp Ala Cys Leu Gly Gln Val Thr Gly Glu Glu Asp Ser Ala Leu Gly
            100                 105                 110

AGA ACG GGC CCC ACC CTG GCC ATG AAG AGG TAT TTC CAG GGC ATC CAT     384
Arg Thr Gly Pro Thr Leu Ala Met Lys Arg Tyr Phe Gln Gly Ile His
        115                 120                 125

GTC TAC CTG AAA GAG AAG GGA TAT AGT GAC TGC GCC TGG GAA ATT GTC     432
Val Tyr Leu Lys Glu Lys Gly Tyr Ser Asp Cys Ala Trp Glu Ile Val
130                 135                 140

AGA CTG GAA ATC ATG AGA TCC TTG TCT TCA TCA ACC AGC TTG CAC AAA     480
Arg Leu Glu Ile Met Arg Ser Leu Ser Ser Ser Thr Ser Leu His Lys
145                 150                 155                 160

AGG TTA AGA ATG ATG GAT GGA GAC CTG AGC TCA CCT                     516
Arg Leu Arg Met Met Asp Gly Asp Leu Ser Ser Pro
                165                 170
```

(2) INFORMATION FOR SEQ ID NO:6:

(i) SEQUENCE CHARACTERISTICS:
        (A) LENGTH: 172 amino acids
        (B) TYPE: amino acid
        (D) TOPOLOGY: linear (ii) MOLECULE TYPE: protein (xi) SEQUENCE DESCRIPTION: SEQ ID NO:6:

```
Cys Asp Leu Ser Gln Asn His Val Leu Val Gly Ser Gln Asn Leu Arg
 1               5                  10                  15

Leu Leu Gly Gln Met Arg Arg Leu Ser Leu Arg Phe Cys Leu Gln Asp
            20                  25                  30

Arg Lys Asp Phe Ala Phe Pro Gln Glu Met Val Glu Gly Gly Gln Leu
        35                  40                  45

Gln Glu Ala Gln Ala Ile Ser Val Leu His Glu Met Leu Gln Gln Ser
    50                  55                  60

Phe Asn Leu Phe His Thr Glu His Ser Ser Ala Ala Trp Asp Thr Thr
65                  70                  75                  80

Leu Leu Glu Gln Leu Arg Thr Gly Leu His Gln Gln Leu Asp Asp Leu
                85                  90                  95

Asp Ala Cys Leu Gly Gln Val Thr Gly Glu Glu Asp Ser Ala Leu Gly
```

```
                      100                 105                 110
Arg Thr Gly Pro Thr Leu Ala Met Lys Arg Tyr Phe Gln Gly Ile His
            115                 120                 125

Val Tyr Leu Lys Glu Lys Gly Tyr Ser Asp Cys Ala Trp Glu Ile Val
        130                 135                 140

Arg Leu Glu Ile Met Arg Ser Leu Ser Ser Ser Thr Ser Leu His Lys
145                 150                 155                 160

Arg Leu Arg Met Met Asp Gly Asp Leu Ser Ser Pro
                165                 170
```